(12) United States Patent
Vancamberg et al.

(10) Patent No.: US 11,375,968 B2
(45) Date of Patent: Jul. 5, 2022

(54) METHODS AND SYSTEMS FOR USER AND/OR PATIENT EXPERIENCE IMPROVEMENT IN MAMMOGRAPHY

(71) Applicant: GE Precision Healthcare LLC, Milwaukee, WI (US)

(72) Inventors: Laurence Vancamberg, Poissy (FR); Serge Muller, Guyancourt (FR); Sridharan Pradeepkumar, Bangalore (IN); Muthu Revathy Authavan, Tamil Nadu (IN); Vinay N., Bangalore (IN)

(73) Assignee: GE Precision Healthcare LLC, Milwaukee, WI (US)

( * ) Notice: Subject to any disclaimer, the term of this patent is extended or adjusted under 35 U.S.C. 154(b) by 73 days.

(21) Appl. No.: 16/841,390

(22) Filed: Apr. 6, 2020

(65) Prior Publication Data
US 2021/0307711 A1 Oct. 7, 2021

(51) Int. Cl.
*A61B 6/00* (2006.01)
*A61B 6/02* (2006.01)
*A61B 6/04* (2006.01)

(52) U.S. Cl.
CPC .............. *A61B 6/502* (2013.01); *A61B 6/025* (2013.01); *A61B 6/0414* (2013.01);
(Continued)

(58) Field of Classification Search
CPC ......... A61B 6/502; A61B 6/465; A61B 6/545; A61B 6/025; A61B 6/0435; A61B 6/5205; A61B 6/0414; A61B 6/547; A61B 6/468; A61B 2562/02; A61B 6/022; A61B 6/462; A61B 6/463; G06T 2207/30068; G06T 7/30; G16H 40/40
See application file for complete search history.

(56) References Cited

U.S. PATENT DOCUMENTS

| 6,354,502 | B1 | 3/2002 | Hagstrom et al. |
| 7,558,367 | B1 * | 7/2009 | Tinwala ................. G01G 19/52 378/37 |

(Continued)

FOREIGN PATENT DOCUMENTS

| CN | 104127196 A | 11/2014 |
| CN | 105748161 A | 7/2016 |

(Continued)

OTHER PUBLICATIONS

DE102014206005-Abstract; Machine Translation obtained from Espacenet.com, Oct. 12, 2021.
(Continued)

*Primary Examiner* — Dani Fox
*Assistant Examiner* — Soorena Kefayati

(57) ABSTRACT

Various methods and systems are provided for breast positioning assistance during mammography and image guided interventional procedures. In one example, a vision system is utilized to evaluate one or more of a patient position, a breast position, and breast anatomy to determine if the patient and breast are adjusted to desired positions preferred for a desired view and imaging procedure. Further, based on the evaluation, prior to acquiring x-ray images, real-time feedback may be provided to guide the user to position the breast and/or the patient.

19 Claims, 12 Drawing Sheets

(52) U.S. Cl.
CPC ............ *A61B 6/0435* (2013.01); *A61B 6/465* (2013.01); *A61B 6/5205* (2013.01); *A61B 6/545* (2013.01); *A61B 6/468* (2013.01); *A61B 6/547* (2013.01); *A61B 2562/02* (2013.01)

(56) References Cited

U.S. PATENT DOCUMENTS

| | | | |
|---|---|---|---|
| 7,968,847 B2 | 6/2011 | Oelschlegel et al. | |
| 7,974,378 B2* | 7/2011 | Fischer | A61B 6/08 378/205 |
| 11,076,820 B2* | 8/2021 | Smith | A61B 6/542 |
| 2010/0208037 A1* | 8/2010 | Sendai | A61B 6/463 348/51 |
| 2011/0004347 A1* | 1/2011 | Hornig | A61B 6/502 700/275 |
| 2011/0305313 A1* | 12/2011 | Sklansky | A61B 6/502 378/37 |
| 2012/0051501 A1* | 3/2012 | Nakayama | A61B 6/589 378/62 |
| 2012/0150034 A1* | 6/2012 | DeFreitas | A61B 8/483 250/363.04 |
| 2014/0303483 A1* | 10/2014 | Schellenberg | A61B 6/584 600/411 |
| 2015/0265186 A1* | 9/2015 | Kuwabara | A61B 5/708 378/37 |
| 2016/0270751 A1* | 9/2016 | Laukkanen | A61B 6/464 |
| 2017/0055843 A1* | 3/2017 | Umezawa | A61B 5/0091 |
| 2017/0100089 A1* | 4/2017 | Chang | A61B 6/544 |
| 2017/0265828 A1* | 9/2017 | Tsujii | A61B 5/0091 |
| 2018/0140270 A1 | 5/2018 | Profio et al. | |
| 2019/0209106 A1* | 7/2019 | Bechtold | G06T 7/70 |
| 2020/0178926 A1* | 6/2020 | Kshirsagar | A61B 6/465 |
| 2020/0261048 A1* | 8/2020 | Arai | A61B 6/0435 |
| 2020/0305821 A1* | 10/2020 | Sendai | A61B 6/487 |

FOREIGN PATENT DOCUMENTS

| | | |
|---|---|---|
| DE | 102014206005 A1 | 10/2015 |
| EP | 3669784 B1 | 3/2021 |
| FI | 126329 B | 5/2015 |
| JP | 2013528473 A | 7/2013 |

OTHER PUBLICATIONS

EP application 21163742.6 filed Mar. 19, 2021—Extended Search Report dated Aug. 23, 2021; 10 pages.

* cited by examiner

METHODS AND SYSTEMS FOR USER AND/OR PATIENT EXPERIENCE IMPROVEMENT IN MAMMOGRAPHY

FIELD

Embodiments of the subject matter disclosed herein relate to mammography and biopsy procedures, and more particularly, to breast positioning assistance for workflow and user/patient experience improvement during mammography and breast biopsy procedures.

BACKGROUND

Mammography is a medical imaging procedure for detecting one or more cancers of a breast. Accurate interpretation of a mammography image (also known as mammogram) and detection breast cancer relies on generation of high quality mammograms. A key factor affecting the quality of a mammogram is breast positioning. Failure to position the breast properly may result in mammographic artifacts and tissue exclusion, and consequently, missed cancers. The level of training and experience of the technologists can significantly affect image quality. For example, technologists with less/intermediate training and/or experience may not position the breast properly, and as result, recall rates and missed cancers may be higher.

Further, previous approaches for position evaluation involve the technologist reviewing the x-ray image acquired. Consequently, radiation dose is delivered to the patient even if they were not well positioned. Even during x-ray image review, some technologists may not evaluate the x-ray image correctly, which also increases recall rates and reduces confidence in diagnosis.

BRIEF DESCRIPTION

In one embodiment, a method for an x-ray mammography system comprises: evaluating, via vision sensing using one or more cameras coupled to the x-ray mammography system, one or more of a patient position of a patient, a partial view of the patient, and a breast anatomy of the patient; detecting one or more of a patient positioning error and a breast positioning error based on the evaluation; and providing real-time feedback to a user based on the detection via a user interface of the mammography system. In this way, the vision sensing system may be utilized to evaluate breast position in real-time and provide feedback in real-time to guide the technologist to position the breast to achieve high quality images. By guiding the technologist based on vision sensing, real-time guidance for proper positioning may be provided, which results in improved positioning and high-quality images, and consequently, sensitivity of cancer detection is increased.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1A:
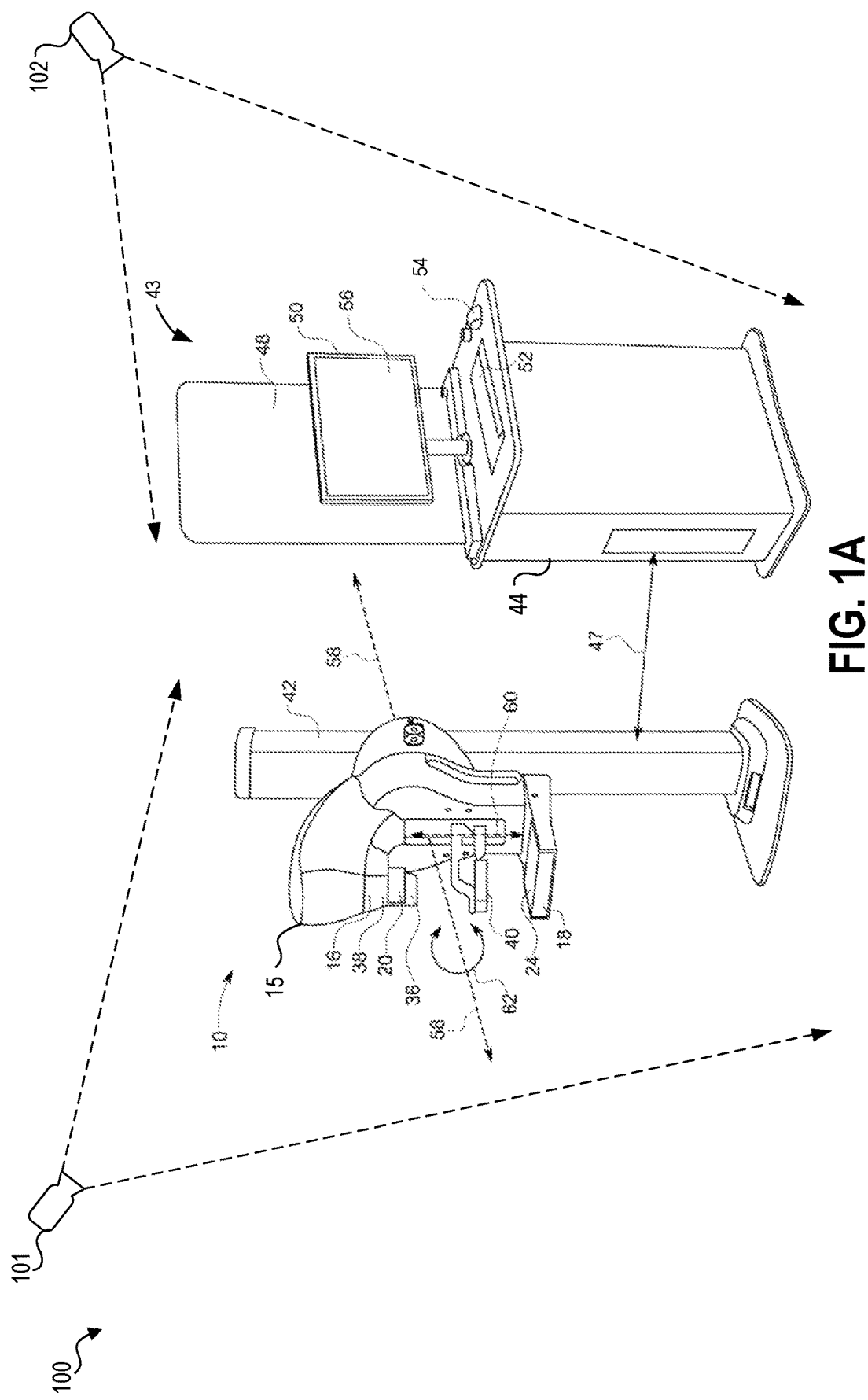
FIG. 1A is a schematic illustration of a mammography system including a vision sensing system, according to an embodiment of the disclosure.
Figure 1B:
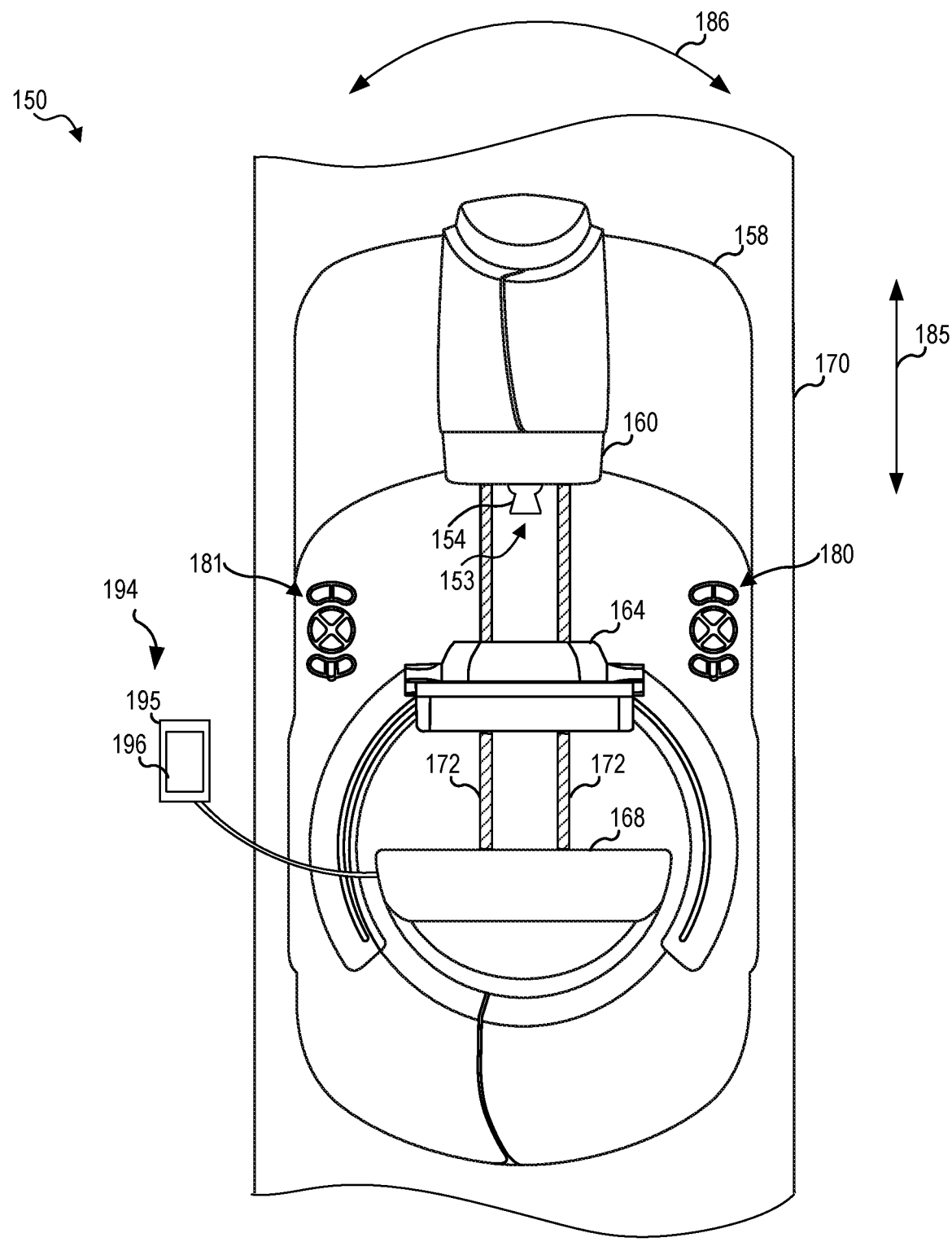
FIG. 1B is a schematic illustration of a front view of a portion of a mammography system including a vision sensor, for detecting one or more of breast position and breast morphology, according to an embodiment of the disclosure.
Figure 1C:
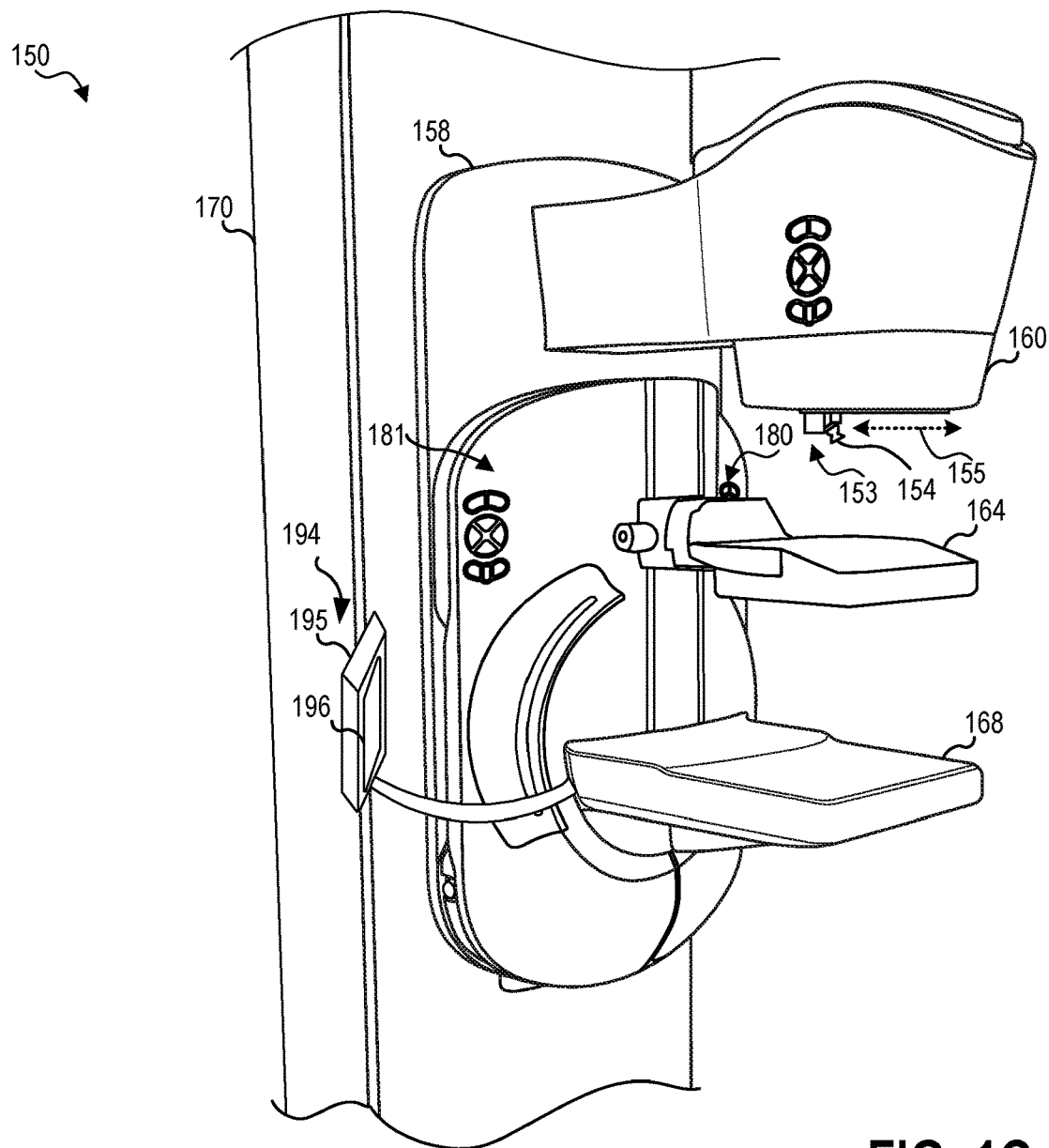
FIG. 1C is a schematic illustration of a perspective view of the mammography system of FIG. 1B including the vision sensor, according to an embodiment of the disclosure.
Figure 1D:
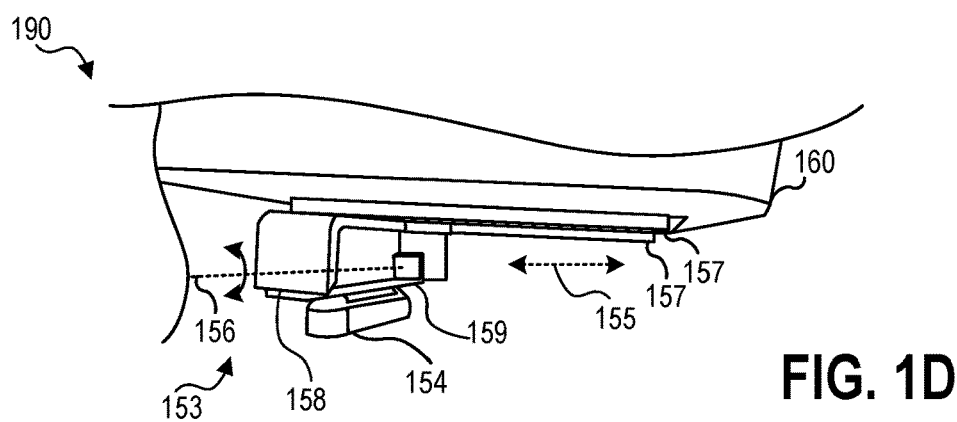
FIG. 1D is a schematic illustration of an enlarged perspective view of a portion of a gantry of the mammography system of FIG. 1B, showing an exemplary positioning of a vision sensor for detecting one or more of breast position and breast morphology, according to an embodiment of the disclosure.
Figure 2:
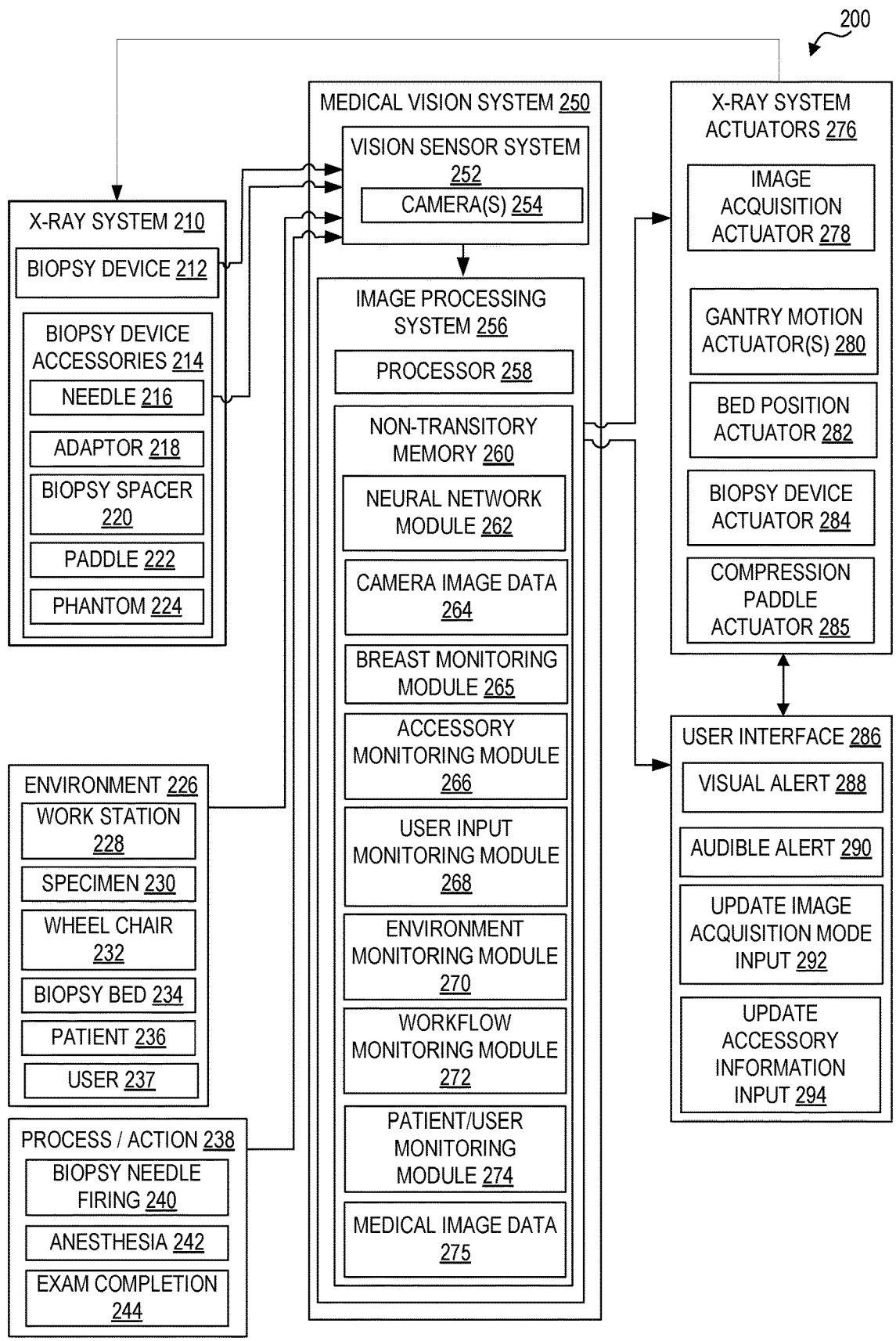
FIG. 2 is block diagram of a mammography system including a vision monitoring system, illustrating a plurality of objects sensed by the vision system and a plurality of actuators controlled based on the objects sensed, according to an embodiment of the disclosure.
Figure 7:
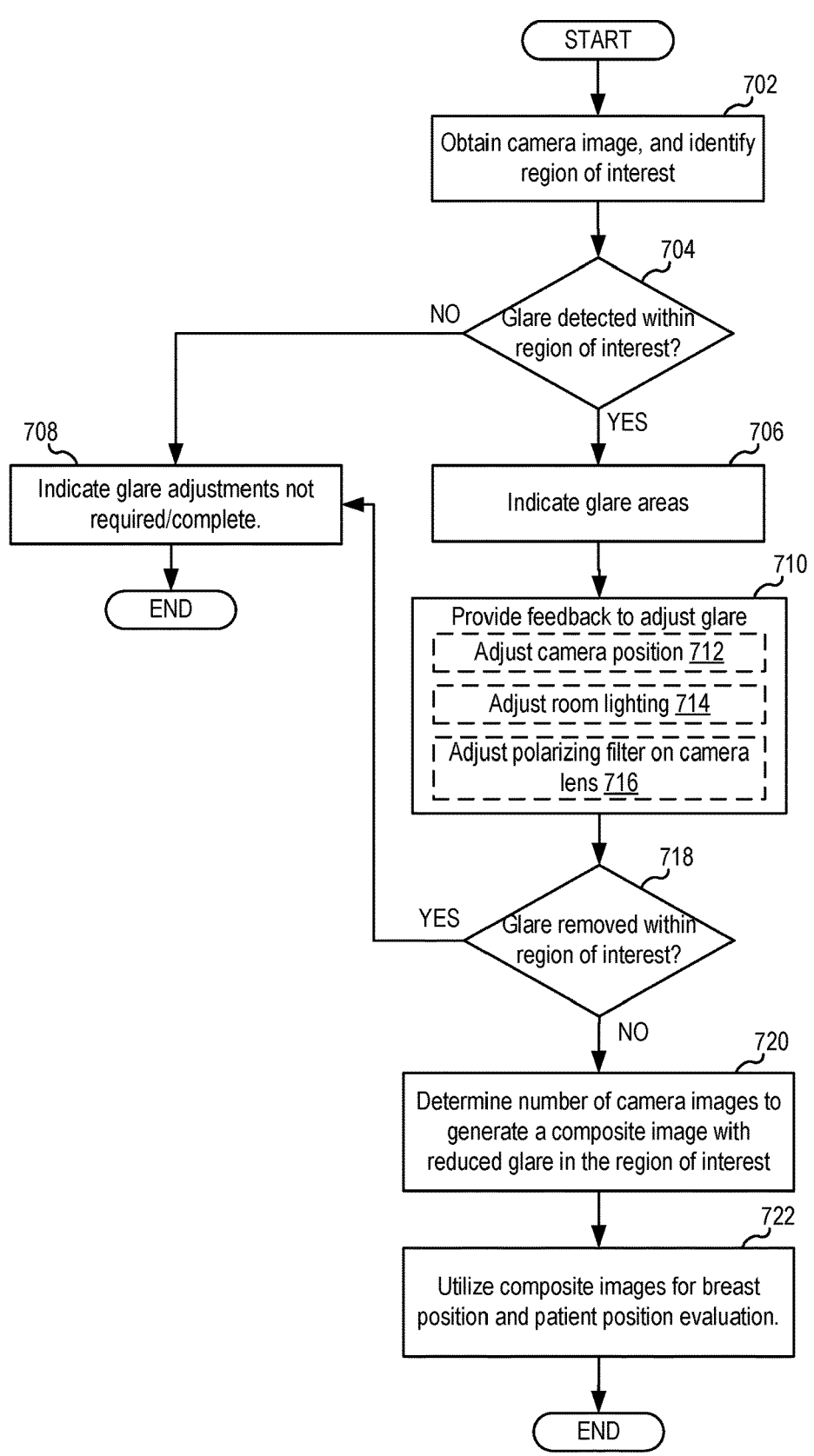
FIG. 7 is a high-level flow chart illustrating a method for reducing glare from one or more camera images obtained with one or more vision sensors coupled to a mammography system, according to an embodiment of the disclosure.
Figure 8A:
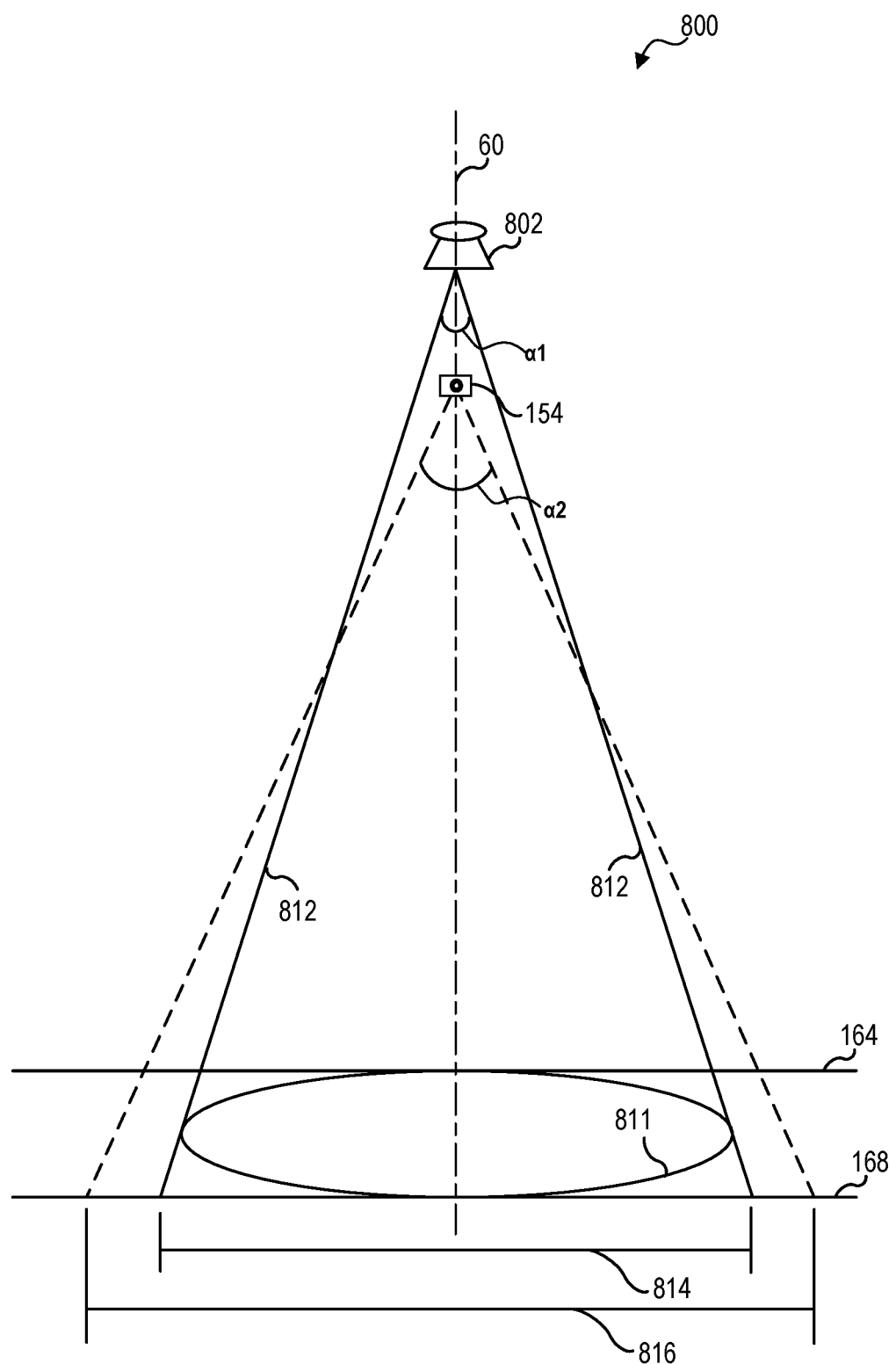
FIG. 8A is an illustration showing an example positioning of an x-ray source of an x-ray mammography system and a vision sensor for craniocaudal (CC) view evaluation, according to an embodiment of the disclosure.
Figure 8B:
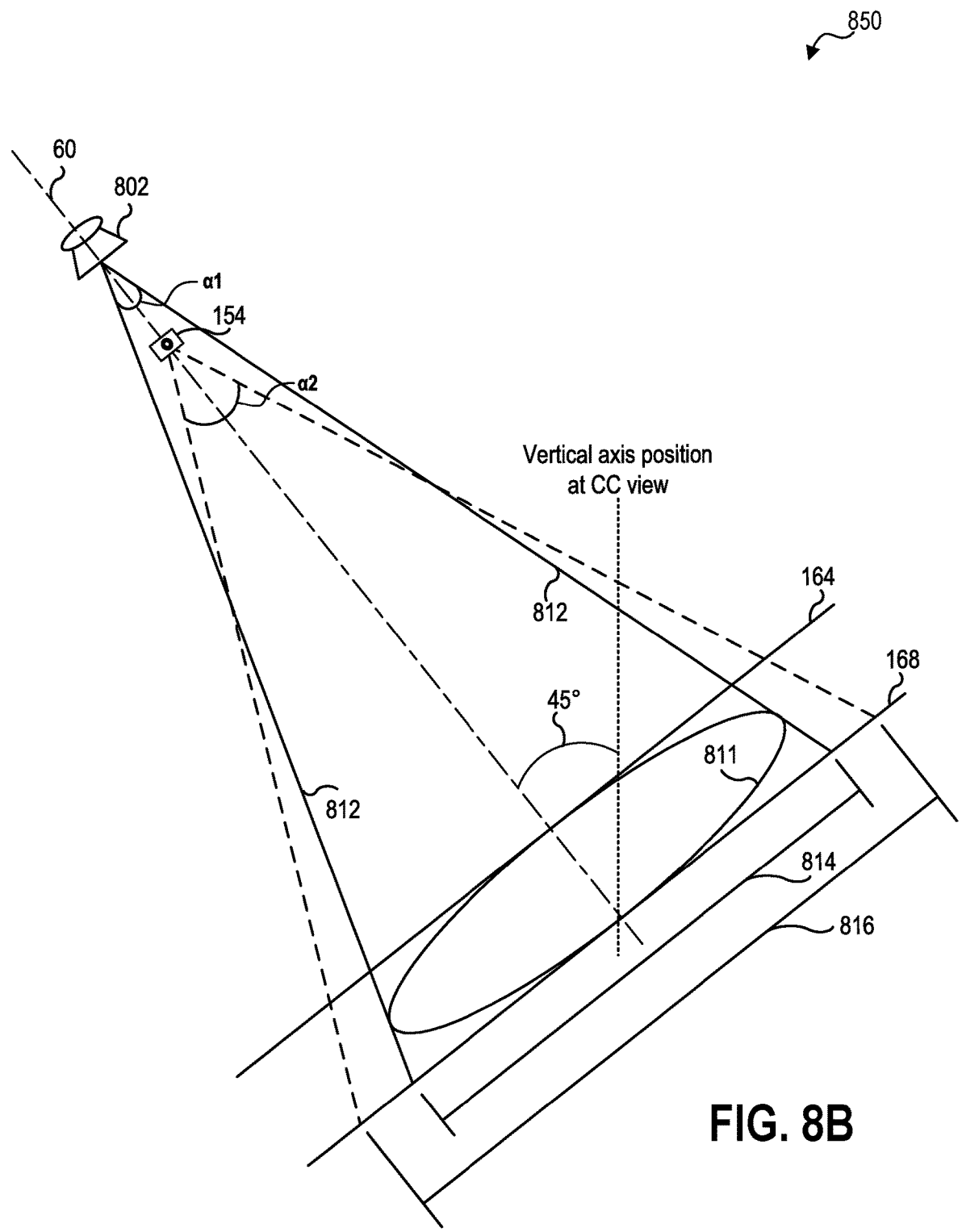
FIG. 8B is an illustration showing an example positioning of an x-ray source of an x-ray mammography system and a vision sensor for mediolateral oblique (MLO) view evaluation, according to an embodiment of the disclosure.

The following description relates to various embodiments for an x-ray system for mammography and biopsy procedures. An exemplary embodiment of an x-ray system is shown at FIG. 1A, which includes a vision system, including one or more cameras, to detect one or more of accessories associated with each procedure, the body part involved in the procedure, one or more objects in the environment surrounding the system, a patient, and a user. Based on the detection, the x-ray system including the vision system, may evaluate one or more of a breast morphology, a breast position, a patient morphology, a patient position, a user morphology, and a user position. An exemplary embodiment of the vision system for evaluating breast position is illustrated at FIG. 1B. Specifically, the vision system may include a camera coupled to a gantry of the x-ray system such that a field of view of the camera is in alignment with an x-ray field of view. Exemplary position of the camera is further illustrated at FIGS. 1C and 1D. A block diagram of one or more objects and actions detected by the vision system, including the camera, and one or more actuators of the x-ray system adjusted based on the one or more objects and actions detected is illustrated at FIG. 2. A controller of the x-ray mammography system may be configured to evaluate one or more of a breast position and breast morphology, a patient position and patient morphology, and a user position and user morphology based on a mode of operation of the x-ray system, as illustrated with a high-level flow chart at FIG. 3. Specifically, the vision system may include at least a first vision sensor and a second sensor that are utilized for evaluating patient position and breast position respectively. Exemplary positions of the second vision sensor with respect to the x-ray source for CC view and MLO view are illustrated at FIGS. 8A and 8B respectively. Further, the controller may include instructions to evaluate breast position and patient position with respect to the x-ray system, and provide real-time feedback to the user during a mammography procedure, as discussed at FIGS. 4A and 4B. Furthermore, exemplary methods for breast position and patient position evaluation, and real-time feedback for breast position adjustment during DBT are described at FIGS. 5 and 6. Further still, the controller may include instructions to reduce glare within an area of interest of one or more camera images obtained with the vision system, as shown at FIG. 7.

During an imaging procedure, such as mammography or DBT imaging procedure, and during an image-guided interventional procedure, such as DBT-guided biopsy, CESM biopsy, stereotactic biopsy, etc., positioning the breast plays an important part in obtaining high quality images that demonstrate the various areas of the breast. Further, depending on the view, some of the landmarks for positioning may differ. Typically, the determination of whether the breast is positioned to provide high quality mammograms cannot be made until the mammogram is obtained. The inventors herein have identified the above-mentioned issues and provide methods and systems for improving positioning of breast prior to initiating acquisition. In particular, methods and systems are provided for evaluating breast position and patient body position prior to imaging, and providing real-time feedback for improving breast and patient positioning. In one embodiment, a first vision sensor, used for evaluating the patient body position, captures an image of the patient and the x-ray system, and a second vision sensor, used for evaluating breast position, captures a compressed breast image. The camera images obtained from the first and the second vision sensors are then input into an artificial intelligence (AI) based image processing model, which evaluates the input camera images for a desired breast positioning framework (that is, for inclusion of breast anatomical landmarks based on the view), and further evaluates patient position, and provides real-time feedback to the technologist/user for one or more of patient and breast position correction, through the user interface. Details of evaluating one or more of patient position and breast position for improving breast position for imaging with the mammography system are further described below.

Referring to FIG. 1A, a mammography system 100 including an x-ray system 10 for performing a mammography procedure is shown, according to an exemplary embodiment. The x-ray system 10 may be a tomosynthesis system, such as a digital breast tomosynthesis ("DBT") system. The x-ray system 10 may be used to perform one or more procedures including digital tomosynthesis imaging, and DBT guided breast biopsy. Further, the x-ray system 10 may be utilized to perform a mammography imaging procedure, wherein one or more views including a craniocaudal (CC view) and a mediolateral oblique (MLO view) of a breast are obtained. The x-ray system may be further used to perform other x-ray screening and diagnostic imaging procedures, including CESM, and contrast enhanced DBT (CE-DBT) diagnostic imaging, and interventional procedures, including CESM-guided biopsy and stereotactic procedures.

The x-ray system 10 includes a support structure 42, to which a radiation source 16, a radiation detector 18, and a collimator 20 are attached. The radiation source 16 is housed within a gantry 15 that is movably coupled to the support structure 42. In particular, the gantry 15 may be mounted to the support structure 42 such that the gantry 15 including the radiation source 16 can rotate around an axis 58 in relation to the radiation detector 18. An angular range of rotation of the gantry 15 housing the radiation source 16 indicates a rotation up to a desired degree on either directions about a vertical axis perpendicular to a horizontal detection surface of the detector 18. For example, the angular range of rotation of the radiation source 16 may be −θ to +θ, where θ may be such that the angular range is a limited angle range, less than 360 degrees. An exemplary x-ray system may have an angular range of ±11 degrees, which may allow rotation of the gantry (that is rotation of the radiation source) from −11 degrees to +11 degrees about an axis of rotation of the gantry. The angular range may vary depending on the manufacturing specifications. For example, the angular range for DBT systems may be approximately ±11 degrees to ±60 degrees, depending on the manufacturing specifications.

The radiation source 16 is directed toward a volume or object to be imaged, and is configured to emit radiation rays at desired times and to acquire one or more images. The radiation detector 18 is configured to receive the radiation rays via a surface 24. The detector 18 may be any one of a variety of different detectors, such as an x-ray detector, digital radiography detector, or flat panel detector. The collimator 20 is disposed adjacent to the radiation source 16 and is configured to adjust an irradiated zone of an object imaged.

In some exemplary embodiments, the system 10 may further include a patient shield 36 mounted to the radiation source 16 via face shield rails 38 such that a patient's body part (e.g., head) is not directly under the radiation. The system 10 may further include a compression paddle 40, which may be movable upward and downward in relation to the support structure 42 along a vertical axis 60. Thus, the compression paddle 40 may be adjusted to be positioned closer to the radiation detector 18 by moving the compression paddle 40 downward toward the detector 18, and a distance between the detector 18 and the compression paddle 40 may be increased by moving the compression paddle upward along the vertical axis 60 away from the detector. The movement of the compression paddle 40 may be adjusted by a user via compression paddle actuator (not shown) included in the x-ray system 10. The compression paddle 40 may hold a body part, such as a breast, in place against the surface 24 of the radiation detector 18. The compression paddle 40 may compress the body part, and hold the body part still in place while optionally providing apertures to allow for insertion of a biopsy needle, such as a core needle, or a vacuum assisted core needle. In this way, compression paddle 40 may be utilized to compress the body part to minimize the thickness traversed by the x-rays and to help reduce movement of the body part due to the patient moving. The x-ray system 10 may also include an object support (not shown) on which the body part may be positioned.

The mammography system 100 may further include workstation 43 comprising a controller 44 including at least one processor and a memory. The controller 44 may be communicatively coupled to one or more components of the x-ray system 10 including one or more of the radiation source 16, the radiation detector 18, the compression paddle 40, and a biopsy device. In one exemplary embodiment, the communication between the controller and the x-ray system 10 may be via a wireless communication system. In other exemplary embodiments, the controller 44 may be in electrical communication with the one or more components of the x-ray system via a cable 47. Further, in an exemplary embodiment, as shown in FIG. 1A, the controller 44 is integrated into workstation 43. In other exemplary embodiments, the controller 44 may be integrated into one or more of the various components of the system 10 disclosed above. Further, the controller 44 may include processing circuitry that executes stored program logic and may be any one of a different computers, processors, controllers, or combination thereof that are available for and compatible with the various types of equipment and devices used in the x-ray system 10.

The workstation 43 may include a radiation shield 48 that protects an operator of the system 10 from the radiation rays emitted by the radiation source 16. The workstation 43 may further include a display 56, a keyboard 52, mouse 54, and/or other appropriate user input devices that facilitate control of the system 10 via a user interface 50.

Further, the x-ray system 10 may include a second control station (not shown) including a second user interface with a second display portion having appropriate input features to facilitate control of the system 10 and view one or more images captured by one or more of the vision system and x-ray system 10. The second control station may be positioned near the x-ray system and may be coupled (wired or wirelessly) to the x-ray system 10. Specifically, the second control station may be positioned such that the user, while adjusting breast and/or patient position, can look at the second display portion and/or the second user interface. Thus, the positioning of the second control station may allow the user to simultaneously view the real-time camera feedback and adjust patient and/or breast position. An exemplary second control station is illustrated at FIGS. 1B and 1C.

Through its processors and controllers, the controller 44 may adjust the operation and function of the x-ray system 10. As an example, the controller 44 may provide timing control, as to when the x-ray source 16 emits x-rays, and may further adjust how the detector 18 reads and conveys information or signals after the x-rays hit the detector 18, and how the x-ray source 16 and the detector 18 move relative to one another and relative to the body part. The controller 44 may also control how information, including images 42 and data acquired during the operation, is processed, displayed, stored, and manipulated. The different processing steps, including receiving one or more signals from one or more sensors, receiving user input, evaluating the received signals/input, image processing, determining reconstruction error, outputting operation parameters including error indications, adjusting one or more actuators of the x-ray system to control operation of the x-ray system, performed by the controller 44, may be provided by a set of instructions stored in non-transitory memory of the processor. Information may also be stored in one or more non-transitory memories of controller 44 for later retrieval and use.

Further, as stated above, the radiation detector 18 receives the radiation rays emitted by the radiation source 16. In particular, during imaging with the x-ray system, a projection image of the imaging body part may be obtained at the detector 18. In some exemplary embodiments, data, such as projection image data, received by the radiation detector 18 may be electrically and/or wirelessly communicated to the controller 44 from the radiation detector 18. The controller 44 may then reconstruct one or more scan images based on the projection image data, by implementing a reconstruction algorithm, for example. The reconstructed image may be displayed to the user on the user interface 50 via a display screen 56.

The radiation source 16, along with the radiation detector 18, forms part of the x-ray system 10 which provides x-ray imagery for the purpose of one or more of screening for abnormalities, diagnosis, dynamic imaging, and image-guided biopsy. For example, the x-ray system 10 may be operated in a mammography mode for screening for abnormalities. During mammography, a patient's breast is positioned and compressed between the detector 18 and the compression paddle 40. Thus, a volume of the x-ray system 10 between the compression paddle 40 and the detector 18 is an imaging volume. The radiation source 16 then emits radiation rays on to the compressed breast, and a projection image of the breast is formed on the detector 18. The projection image may then be reconstructed by the controller 44, and displayed via the display portion 50 on the interface 56.

During mammography, the gantry 15 may be adjusted at different angles to obtain images at different orientations, such as a craniocaudal (CC) image and a mediolateral oblique (MLO) view. Further, during obtaining mammography views (e.g., CC and MLO views) the gantry 15, the compression paddle 40, and the detector 18 may be rotated as a single unit about the axis 58. In other examples, the gantry 15 may be rotated about the axis 58 while the compression paddle 40 and the detector 18 remain stationary.

Further, the x-ray system 10 may be operated in a tomosynthesis mode for performing digital breast tomosynthesis (DBT). During tomosynthesis, the x-ray system 10 may be operated to direct low-dose radiation towards the imaging volume (between the compression paddle 40 and the detector 18) at various angles over the angular range of the x-ray system 10. During tomosynthesis, similar to mammography, the breast is compressed between the compression paddle 40 and the detector 18. The radiation source 16 is then rotated from $-\theta$ to $+\theta$, and a plurality of projection images of the compressed breast is obtained at regular angular intervals over the angular range. For example, if the angular range of the x-ray system is ±11 degrees, 22 projection images may be captured by the detector during an angular sweep of the gantry at approximately one every one degree. The plurality of projection images are then processed by the controller 44 to generate a plurality of DBT image slices. The processing may include applying one or more reconstruction algorithms to reconstruct three dimensional DBT image of the breast.

Furthermore, the x-ray system 10 may be configured to perform a DBT-guided biopsy procedure. Accordingly, in some exemplary embodiments, the system 10 may further include a biopsy device (not shown) comprising a biopsy needle for extracting a tissue sample for further analysis.

In one exemplary embodiment, the biopsy device may include a biopsy table (not shown) that is positioned over the detector 18 of the x-ray system 10. For example, the biopsy table may be configured to slide over the detector 18. During set-up of the biopsy device, the user may remove the compression paddle 40 of the x-ray system 10, and slide the biopsy table over the detector 18. Upon positioning the biopsy device on the x-ray system 10, a suitable compression paddle for biopsy (not shown), such as a horizontal approach biopsy plate (without aperture) or a vertical approach biopsy plate (with aperture), depending on the type of biopsy, may be selected and coupled to the x-ray system 10.

The biopsy device may further include a biopsy tool interface having a biopsy tool display. The biopsy tool interface may be coupled to the biopsy table via a communication port. In one embodiment, the biopsy tool interface may be communicatively coupled with the x-ray system controller 44, and as such, the user may be able to adjust a position of the x-ray system, such as adjusting the gantry to a park position, via the biopsy tool interface. In other embodiments, the biopsy tool interface may be coupled to a biopsy device controller, which sends and receives information to and from the x-ray system controller 44. In some other embodiments, additionally or alternatively, adjustment and control of the biopsy device may be performed by a biopsy device control module of the x-ray system controller 44.

The biopsy device may include a biopsy tool that may be directly coupled to the biopsy table. The biopsy tool may include a biopsy gun holder for mounting a biopsy gun. Further, the biopsy gun holder may include a mechanical stop for adjusting a position of a biopsy needle. The biopsy needle may include an outer cannula, an inner cannula positioned therein, and an opening for receiving a portion of tissue from the biopsied lesion or target. The cannulas form a cutting device wherein the outer cannula is configured to slide or rotate over the inner cannula, and/or the inner cannula is configured to slide or rotate within the outer cannula.

During biopsy, prior to inserting the needle, the breast is positioned between a compression paddle (not shown) and a top surface of the table. In some examples, a breast spacer may be positioned on the surface, and the breast is positioned between the compression paddle and the spacer, and compressed by moving the compression paddle toward the surface. Upon positioning the breast, a first set of targeting images are obtained by the scanning the compressed breast with x-ray system 10 at various angles over its angular range to identify a target for biopsy. The first set of targeting images may be three dimensional images (DBT images) or two-dimensional full field digital mammography images reconstructed from the x-ray system acquisitions. The user may localize the concerned region and identify a target position for biopsy by selecting the target position from the first set of images. The target position may be identified by x, y, and z coordinates within a DBT volume between the compression paddle and the biopsy table surface or spacer (if used). Based on the target position coordinates selected by the user, the biopsy device controller may adjust the mechanical stop position of the biopsy gun holder such that when the needle is inserted into the compressed breast via the biopsy gun, the needle movement is stopped when the needle tip reaches a desired position (referred to as pre-fire position) with respect to the target position. While the present example illustrates adjustment of the biopsy device via the biopsy device controller, it will be appreciated that in some embodiments, the x-ray system controller 44 may command control of the biopsy device.

Once the biopsy tool and the biopsy gun are at target position, the user/radiologist may drive the needle through the biopsy gun until it reaches the mechanical stop. Once fully inserted, the needle is then at the pre-fire position (that is, the position where a notch of the needle is in front of the lesion to puncture). Subsequently, a second set of images with the biopsy needle at the pre-fire position is obtained. The user may then initiate firing of the biopsy needle via the biopsy gun. Once the biopsy needle is fired, at least one biopsy sample may be removed from the body part, such as a patient's breast, by use of aspiration and/or the cutting mechanism formed by the inner and outer cannulas. The sample is moved by aspiration down an aspiration tube coupled to a collection chamber with individual pre-labeled chambers to delineate the order or location of each sample from the biopsy procedure. Alternative means of labeling each sample allowing for location identification and/or order identification may also be employed. Further, after needle firing, a third set of images with the needle in the post-fire position may be obtained.

The mammography system 100 may further include one or more vision sensors for sensing one or more components and accessories of the mammography system 100. The one or more vision sensors may include a first vision sensor 101 and a workstation vision sensor 102, as shown in FIG. 1A. The first vision sensor 101 may be configured to sense one or more components and accessories associated with the x-ray system 10. Further, any of the first vision sensor 101 may be configured to sense one or more user and patient morphology and actions while the workstation vision sensor 102 may be utilized to monitor user position and/or action at the workstation. While the present example, illustrates two cameras for implementing vision sensing for the mammography system 100, it will be appreciated that the vision system may include additional cameras or fewer camera, as discussed further below. Further, one or more vision sensors may include a second vision sensor (not shown at FIG. 1A) coupled to the x-ray system 10. The second vision sensor may be utilized for capturing camera images of the compressed breast in the imaging volume. As such, camera images obtained with the second vision sensor may be utilized for evaluating breast position prior to acquiring x-ray projection images. Details of the location and adjustment of second vision sensor for breast position evaluation are described below at FIGS. 1B, 1C, and 1D.

An exemplary embodiment of a vision system including a camera for monitoring breast position and breast morphology with respect to the field of view of an x-ray system 150 is shown at FIG. 1B. Specifically, a vision sensor system 153 including a second vision sensor 154 is shown. X-ray system 150 is similar to x-ray system 10 discussed at FIG. 1A, and hence the description of similar components and elements will not be repeated here for the sake of brevity. Briefly, x-ray system 150 includes a gantry 158 comprising a radiation source 160, a radiation detector 168, and a collimator (not shown) coupled to a support structure 170. The x-ray system 150 further includes a compression paddle 164 for holding a body part, such as a breast, in place against a top surface of the radiation detector 168. The compression paddle 164 may be coupled to a support rail 172 of the gantry 158, and is movable upward and downward along the support rail in a direction away and toward the radiation detector 168. The movement of the gantry 158 and the compression paddle 164 may be controlled via respective actuators based on signals from a controller (not shown), such as a controller 44 at FIG. 1A, communicatively coupled to the x-ray system 150. The gantry 158 may rotate clockwise and anticlockwise to a desired degree about a vertical axis of the support structure. Rotation movement of the gantry 158 is indicated by double-ended arrow 186. Further, a gantry height may be adjusted by moving the gantry 158 vertically upward and downward, as indicated by double-ended arrow 185.

The second vision sensor 154 may be coupled to the gantry 158 such that a field of view of the second vision sensor 154 is in alignment with respect to the field of view of the x-ray system 150, particularly with respect to the radiation source located within the gantry 158. The second vision sensor 154 may be used to monitor breast position and breast anatomical landmarks of the patient during a procedure, such as mammography imaging, DBT imaging, or image-guided biopsy, performed by the x-ray system 150. In one example, the second vision sensor 154 may be configured as an RGB-D camera that combine depth information with RGB color information. Further, the second vision sensor 154 may be communicatively coupled to a controller of the x-ray system 150, and one or more camera images and camera image sequences captured by the second vision sensor 154 may be stored in a non-transitory memory of the controller. Further, the second vision sensor 154 may be configured to capture movements and/or action. For example, a sequence of camera images over a duration may be obtained, which may be used for action recognition.

In some embodiments, the second vision sensor 154 may be positioned so as to monitor and evaluate a partial portion of the patient in addition to compressed breast position. That is, the second vision sensor may also be used to capture partial portions of the patient (e.g., patient shoulder) and thus, provide a partial view of the patient in addition to views of compressed breast.

It will be appreciated that in some embodiments the second vision sensor may be positioned such that the imaging volume including the compression paddle, the detector, and the compressed breast is visualized via the second vision sensor 154.

Taken together, the second vision sensor 154 may be adjusted (e.g., by adjusting a position of the vision sensor 154) to view and/or capture one or more of the imaging volume (including the compression paddle, the detector, and the compressed breast), the imaging volume and a margin volume, and the imaging volume and a partial portion of the patient.

Further, the x-ray system 150 may include a second control station 194 including a second user interface 195 having a second display portion 196 having appropriate input features to facilitate control of the system 150 and view one or more images captured by one or more of the vision system 153 and x-ray system 150. The second control station 194 may be positioned near the x-ray system 150 and is shown coupled to the x-ray system 10. Real-time feedback, as discussed herein, for adjusting one or more of patient position, breast position, and x-ray system position (e.g., gantry position) may be provided to the user via the second control station 194. That is, via the second display 196 of the second user interface 195. In this way, while adjusting breast and/or patient position, the user can easily view the feedback via the second display portion 195 of the second user interface 195. Thus, the positioning of the second control station 194 close to the x-ray system 150 may allow the user to simultaneously view the real-time camera feedback and adjust patient and/or breast position.

While the present example shows the second control station 194 positioned on one side of the x-ray system 150, a third control station, similar to the second control station 194 may be positioned on the opposite side of the x-ray system. Further, the second control station 194 may be removable coupled to the x-ray system 150. Thus, when desired, the second control station may be removed and positioned on the opposite side.

Further, in one example, the camera images captured by the second vision sensor 154 may be pre-processed to reduce glare and extract relevant image data, and the processed image data may be used as input into an artificial intelligence based deep learning model (stored in a controller, an edge device connected to the controller, a cloud in communication with the controller, or any appropriate combination thereof) comprising a neural network such as a convoluted neural network for evaluating breast position based on breast anatomical landmarks detected during positioning of the breast for various imaging and image-guided procedures with the x-ray system 150. Some of the breast anatomical landmarks (also referred to as breast structures) may vary depending on the view (e.g., CC or MLO view) and procedure (e.g., mammography or DBT), while there may be some common breast anatomical landmarks or breast structures that are evaluated for breast positioning at each view. Details of evaluating breast position based on the anatomical landmarks identified or detected with the second vision sensor 154 are further discussed below at FIGS. 2-6.

Further, the second vision sensor 154 may be positioned on the gantry 158 such that a field of view of the second vision sensor 154 encompasses the compression paddle 164 and the imaging volume between the compression paddle 164 and the detector 168. One or more images from the camera may be used to detect the rims of the compression paddle, and detect one or more of contours, openings, recesses, bends, and textures on the portion of the compression paddle between the rims of the compression paddle. Based on the detected attributes of the compression paddle, the vision system may determine a type of compression paddle used with the mammography system.

An exemplary positioning of the second vision sensor 154 is further illustrated with respect to FIG. 1C. Specifically, FIG. 1C shows a perspective view of the x-ray system 150. The second vision sensor 154 is positioned on a housing of radiation source 160 via a pair of rails such that the camera is movable along an axis 155 in forward and backward directions as indicated by arrow 155. An enlarged portion 190 of the x-ray system including the vision sensor 154 is shown at FIG. 1D. The second vision sensor 154 is mounted on a pair of rails 157, and movable along axis 155, and rotatable about an axis 156 perpendicular to axis 155. In one example, the camera position may be adjusted, via rotation along 156 and/or movement along 155, such that a field of view of the first camera 154 is in alignment with the field of view of the radiation source 160. In one example, the second vision sensor 154 may be integrated with the x-ray system 150. In other examples, the vision system 153 may be an ad-hoc system that may be removably coupled to the x-ray system when needed.

Returning to FIG. 1A, the one or more vision sensors may be communicatively coupled to the controller 44. Details of the various components of the mammography system 100 that may be sensed and monitored by the first vision sensor 101 and workstation vision sensor 102, and the various actuators of the mammography system 100 that may be adjusted in response to the sensing and monitoring by the cameras will be further elaborated with respect to FIG. 2 below.

Turning to FIG. 2, a block diagram of a mammography system 200 is shown. The mammography system 200 may be a non-limiting example of the mammography system 100 at FIG. 1. Briefly, the mammography system 200 may be utilized to perform one or more of a mammography procedure, such as a routine mammogram, a digital breast tomosynthesis, and a biopsy procedure, such as a stereotactic biopsy or DBT-guided biopsy. The mammography system 200 may include a medical vision system 250 having at least a vision sensor system 252 and a processing system 256 to perform one or more of sensing, monitoring, and analyzing of one or more accessories and components associated with the mammography system 200. Further, the mammography system 200 may be automatically adjusted, controlled, and set-up via the processing system 256 based on the input from the vision sensor system 252 and the analysis of the input by the processing system 256, to improve workflow, breast positioning, and patient positioning, during one or more of the mammography and biopsy procedures performed with the mammography system 200. The processing system 256 may be an non-limiting example of controller 44 at FIG. 1, and may be configured to receive signals form one or more sensor systems of the mammography system 200, including the vision sensor system 252, as further discussed below. The processor may be further configured to analyze the data received from the sensor systems, and adjust operation of the mammography system 200 via one or more x-ray system actuators 276, in addition to providing real-time feedback including one or more alerts and indications to one or more of the user and the patient via a user interface 286 of the mammography system 200 as further discussed below.

The mammography system 200 may include an x-ray system 210, and a medical vision system 250. X-ray system 210 may be an example of x-ray system 10 discussed at FIG. 1A, or x-ray system 150 at FIG. 1B. In one exemplary embodiment, the x-ray system 210 may be configured as a medical imaging modality for performing a mammography procedure to image and analyze a body part of a patient, such as a breast. In another exemplary embodiment, the x-ray system 210 may be configured for performing a biopsy procedure, such as an x-ray guided biopsy to obtain a tissue sample from the body part of the patient. Further, the x-ray system 210 may be converted from a mammography system for obtaining medical scan images to a biopsy system to perform a biopsy procedure for extracting tissue for evaluation. When the x-ray system 210 is utilized to perform a biopsy procedure, a biopsy device 212 may be coupled to the x-ray system 210. The biopsy device 212 may be an example of the biopsy device described at FIG. 1A, and may include a biopsy table, a biopsy tool, a biopsy tool interface, a biopsy gun holder, and a biopsy gun. Further, the biopsy device 212 may include one or more biopsy device accessories 214 coupled to one or more of the x-ray system 210 and the biopsy device 212. The one or more biopsy device accessories 214 may include a needle 216 for entering the body part and extracting a tissue portion for further analysis by a clinician, an adaptor 218, a biopsy spacer 220 for use as a support for the body part and to obtain desired positioning of the body part with respect to the needle 216 during biopsy, a compression paddle 222 for supporting the body part and holding the body part so as to reduce movement during biopsy, and one or more phantom 224 for performing quality check prior to mammography or biopsy. The compression paddle 222 is an example of compression paddle 40 described with respect to FIG. 1A or compression paddle 164 at FIG. 1B. The mammography system may be configured to monitor, via the medical vision system 250, one or more of components, such as the biopsy device 212, different components of the biopsy device 212, and accessories, such as biopsy device accessories 214.

In one exemplary embodiment, the vision system 250 may be utilized to detect the presence of the compression paddle 222. Further, upon detecting the compression paddle, the vision system 250 may generate one or more images of the compression paddle 222. The one or more images of the compression paddle 222 may then be utilized to identify a type/classification of the compression paddle based on one or more attributes of the compression paddle 222.

The one or more attributes of the compression paddle 222 may include a distance between a left rim and a right rim of the paddle, presence or absence of one or more openings/recess on a top surface of the paddle between the left and the right rim, presence or absence of textural difference in the middle of the paddle, presence or absence of one or more bends on the surface of the paddle between the left and the right rims, and shape of the paddle. Based on the detected attributes, the vision system 250 may identify the type of compression paddle attached to the system. For example, the side rims of the compression paddle may be identified, and a distance between the rims may be calculated. Further, based on the one or more images of the compression paddle, the vision system may determine if one or more other attributes of the compression paddle surface between the rims, such as contours, openings, recesses, bends, and/or textures may be detected. The rim distance and the other attributes of the compression paddle may be utilized to identify the type of compression paddle currently used with the mammography system. In some examples, based on the type of compression paddle identified, the vision system 250 may determine a mode of operation. As an example if a compression paddle specific for biopsy is detected (e.g., biopsy paddle), the vision system may determine that the user intends to operate the mammography system in the biopsy mode.

Further, additionally or alternatively, a change in position of the compression paddle 222 may be monitored with the vision system 250. As an example, during a mammography exam or a biopsy exam, in order to adjust breast position, the user may move the compression paddle. The vision system 250 may detect a movement of the compression paddle 222, and after compression, based on the changed position of the compression paddle, the controller may command adjustment of a collimator such that the breast is within the field of view of the x-ray system.

Furthermore, in some embodiments, the vision system may be utilized to determine a final (locked) position of the compression paddle in addition or alternative to user confirmation of compression paddle position via the user interface. The final compression paddle position may indicate that the breast is in position for imaging. In one example, upon confirming the final position of the compression paddle, a breast position of the compressed breast may be evaluated, and as such, a breast position evaluation interface may be launched and breast position evaluation may be performed with the vision system 250. Upon confirming, with the vision system 250, that the compressed breast is in a desired position for imaging, the mammography system may automatically begin x-ray image acquisition of the compressed breast. In another example, upon confirming the final position of the compression paddle, one or more of a breast position and a patient position may be evaluated with the vision system 250. Upon confirming that one or more of the breast position, the patient position, and the user position are at respective desired positions for imaging, the mammography system may automatically begin x-ray image acquisition.

Further, in some embodiments, in addition to evaluating one or more of breast position, patient position, and user position, after x-ray image acquisition, the acquired image may be further evaluated to determine of a plurality of anatomical landmarks of the breast are captured in the x-ray image. As such, breast position evaluation may be performed on the acquired x-ray images in addition to evaluating breast position with the vision sensors prior to initiating image acquisition. In this way, a second evaluation of the breast position after image acquisition may be utilized to determine if the desired tissue portions are imaged, and as a result, number of patient recalls may be reduced.

The mammography system 200 may be further configured to monitor an environment 226 surrounding the x-ray system 210 using the medical vision system 250. The environment 226 may include one or more of a workstation 228, a specimen 230, such as a body part, for imaging, a wheelchair 232 depending on the patient needs, a biopsy bed 234 depending on the type of biopsy performed and the patient physiology, a patient 236, and a user 237. Furthermore, the mammography system 200 may be configured to monitor, via the medical vision system 250, one or more of a process, a movement, and an action with respect to the x-ray system 210 and the environment 226. The movement and/or action may include a patient movement, a user movement, and movement of one or more accessories of the x-ray system.

As indicated above, the medical vision system 250 includes a vision sensor system 252 comprising one or more cameras 254, and an image processing system 256 comprising a processor 258, and a non-transitory memory 260. The vision sensor system 252 may be communicatively coupled to the image processing system 256. Specifically, the processing system 256 may receive one or more signals from the one or more cameras 254 of the vision system. The one or more cameras of the vision system 252 may be similar to cameras 101 and 102 discussed with respect FIG. 1A, and as such, the one or more cameras 254 may sense the mammography system 200 and its components, accessories, and environment. Data from the one or more cameras 254 may be sent to the processing system 256 for further analysis and storage.

In one exemplary embodiment, the vision sensor system 252 including one or more cameras 254 may include two vision sensors (two cameras 101 and 102) as shown in FIG. 1A. In another exemplary embodiment, the vision sensor system 252 may include another vision sensor, such as the second vision sensor 154, coupled to the x-ray system 150 discussed with respect to FIG. 1B.

The processing system 256 includes a processor 258 configured to execute machine readable instructions stored in the non-transitory memory 260. Processor 258 may be single core or multi-core, and the programs executed thereon may be configured for parallel or distributed processing. In some embodiments, the processor 258 may optionally include individual components that are distributed throughout two or more devices, which may be remotely located and/or configured for coordinated processing. In some embodiments, one or more aspects of the processor 258 may be virtualized and executed by remotely-accessible networked computing devices configured in a cloud computing configuration. According to other embodiments, the processor 258 may include other electronic components capable of carrying out processing functions, such as a digital signal processor, a field-programmable gate array (FPGA), or a graphic board. According to other embodiments, the processor 258 may include multiple electronic components capable of carrying out processing functions. For example, the processor 258 may include two or more electronic components selected from a list of electronic components including: a central processor, a digital signal processor, a field-programmable gate array, and a graphic board. In still further embodiments the processor 258 may be configured as a graphical processing unit (GPU) including parallel computing architecture and parallel processing capabilities. Non-transitory memory 260 may store a neural network module 262, camera image data 264, accessory monitoring module 266, user input monitoring module 268, environment monitoring module 270, workflow monitoring module 272, and patient monitoring module 274. Neural network module 262 may include a deep learning module, comprising a plurality of parameters (including weights, biases, activation functions), and instructions for implementing the one or more deep neural networks to receive image data from the vision sensor system 252, and identify one or more of objects corresponding to one or more of the x-ray system components and accessories, and further identify one or more environmental parameters, and further still, identify one or more processes and actions related to one or more of mammography and biopsy. For example, neural network module 262 may store instructions for implementing a deep learning module comprising one or more neural networks, such as a convolutional neural network (CNN). Neural network module 262 may include trained and/or untrained neural networks and may further include various data, or metadata pertaining to the one or more neural networks stored therein. Non-transitory memory 260 may further store a training module (not shown), which comprises instructions for training one or more of the deep neural networks stored in neural network module 262. The training may be performed with a training data set including camera images of compressed breast, camera images of phantom, and camera images recreated from x-ray images of compressed breast.

Furthermore, using input from the vision sensor system 252, the deep learning module may identify a breast position, breast anatomical landmarks, patient position, patient morphology, user position, and user morphology. Further, using input from the vision sensor system 252, the deep learning module may evaluate breast position as well as patient position and determine one or more errors based on the evaluation. The one or more errors may include a breast positioning error, a patient positioning error, and a user error, and control the mammography system based on the error (e.g., inhibit image acquisition in response to detecting one or more error) and provide real-time based on the errors detected (e.g., as the breast is positioned, the vision sensor may obtain one or more images, which may be utilized to analyze the breast position and morphology, and provide real-time feedback based on the analysis).

In one example, a first deep learning model may include parameters for desired patient position, including a whole body patient position, and a patient position with respect to the x-ray system, where the desired patient position is based on the imaging mode of the x-ray system and a desired view to be acquired by the imaging system. Further, a second deep learning model may include parameters for desired breast position, including one or more compressed breast features included in the imaging volume of the x-ray system, where the desired breast position is based on the imaging mode of the x-ray system and a desired view to be acquired by the imaging system. Prior to initiating x-ray image acquisition, the vision sensor system 252, may be utilized to evaluate current patient position (with respect to the first model) and current breast position (with respect to the second model), and real-time feedback may be provided to the user, via the user interface, based on the evaluation. When the current patient position is in agreement with the first model and the current breast position is in agreement with the second model, x-ray image acquisition may be initiated. Details of evaluating breast position and patient position prior to image acquisition will be further elaborated below with respect to the methods described at FIGS. 2-8B.

Non transitory memory 260 may further store camera image data 264. Camera image data 264 may include images captured by the vision sensor system 252. For example, images captured by the vision sensor may include images of the one or more mammography system, including x-ray system 210 including its components and accessories, the environment 226, and processes and/or actions associated with the x-ray system 210 and the environment 226. Camera image data 264 may further include patient monitoring images, user monitoring images, and compressed breast images.

Non-transitory memory 260 may further store the accessory monitoring module 266 including instructions for monitoring and analyzing the presence and current positions of the one or more accessories 214 and biopsy device 212.

Non-transitory memory 260 may further store the user input monitoring module 268 including instructions for monitoring and analyzing user input via a user interface.

Non-transitory memory 260 may further store the environment monitoring module 270 including instructions for monitoring and analyzing the environment 226, and may store workflow monitoring module 272 including instructions for monitoring and analyzing one or more process and action 238. Further still, non-transitory memory 260 may store patient monitoring module 274 for monitoring and analyzing one or more of patient presence, patient position, and patient movement into and out of the examination room. Additionally, non-transitory memory 260 may store a user monitoring module for monitoring and analyzing one or more of user presence, user position, and user movement into and out of the examination room.

Non-transitory memory 260 may further store medical image data 275. The medical image data 275 may include scan images of the body part captured by the x-ray system 210.

Upon sensing and analyzing one or more of the x-ray system 210, the environment 226, and process and action 238, the image processing system 256 may output instructions to one or more x-ray system actuators 276 based on the sensing and the analyzing. The x-ray system actuators 276 may include image acquisition actuator 278 for controlling a radiation source output from a radiation source such as radiation source 16 at FIG. 1, gantry motion actuators 280 for controlling gantry position of the x-ray system 210, and a bed position actuator for adjusting a biopsy bed position, for example, based on presence or absence of an object in the environment 226 such as the wheel chair 232. The gantry motion actuator(s) 280 may include one or more actuators for adjusting one or more of a gantry lift, a gantry rotation, and a gantry angulation, where the gantry lift motion includes movement of the gantry in an upward or downward direction along the vertical axis of the x-ray system 210, the gantry rotation is the rotation of the detector and the x-ray generation tube around a rotation axis, and the gantry angulation is the rotation of the x-ray tube while the detector remains still within an angular range of rotation.

The x-ray system actuators 276 may further include a biopsy device actuator for adjusting operation of the biopsy device, such as firing of the biopsy needle, for example, based on sensing one or more inconsistencies between the user input and the actual x-ray system configuration as further detailed below. The x-ray system actuators 276 may further include a compression paddle actuator 285 for adjusting movement of the compression paddle 222.

Further, upon sensing and analyzing one or more of the x-ray system 210, breast position, patient position, the environment 226, and process and action 238, the image processing system 256 may output one or more alerts, including real-time feedback, via a user interface 286. The user interface 286 may be an example of user interface 56 at FIG. 1A. The one or more alters output by the processing system 256 via the user interface 286 may include one or more of a visual alert 288 and an audible alert 290. Other types of alerts, such as haptic alerts, are also within the scope of the disclosure. Further, the processing system 256 may be configured to update image acquisition input 292 on the user interface 286 and adjust one or more of x-ray system set-up, configuration, and operation accordingly. Further still, the processing system may be configured to update accessory information input 294 on the user interface 286 and adjust x-ray system set-up, configuration, and operation accordingly.

It should be understood that image processing system 256 shown in FIG. 2 is for illustration, not for limitation. Another appropriate image processing system may include more, fewer, or different components.

Figure 3:
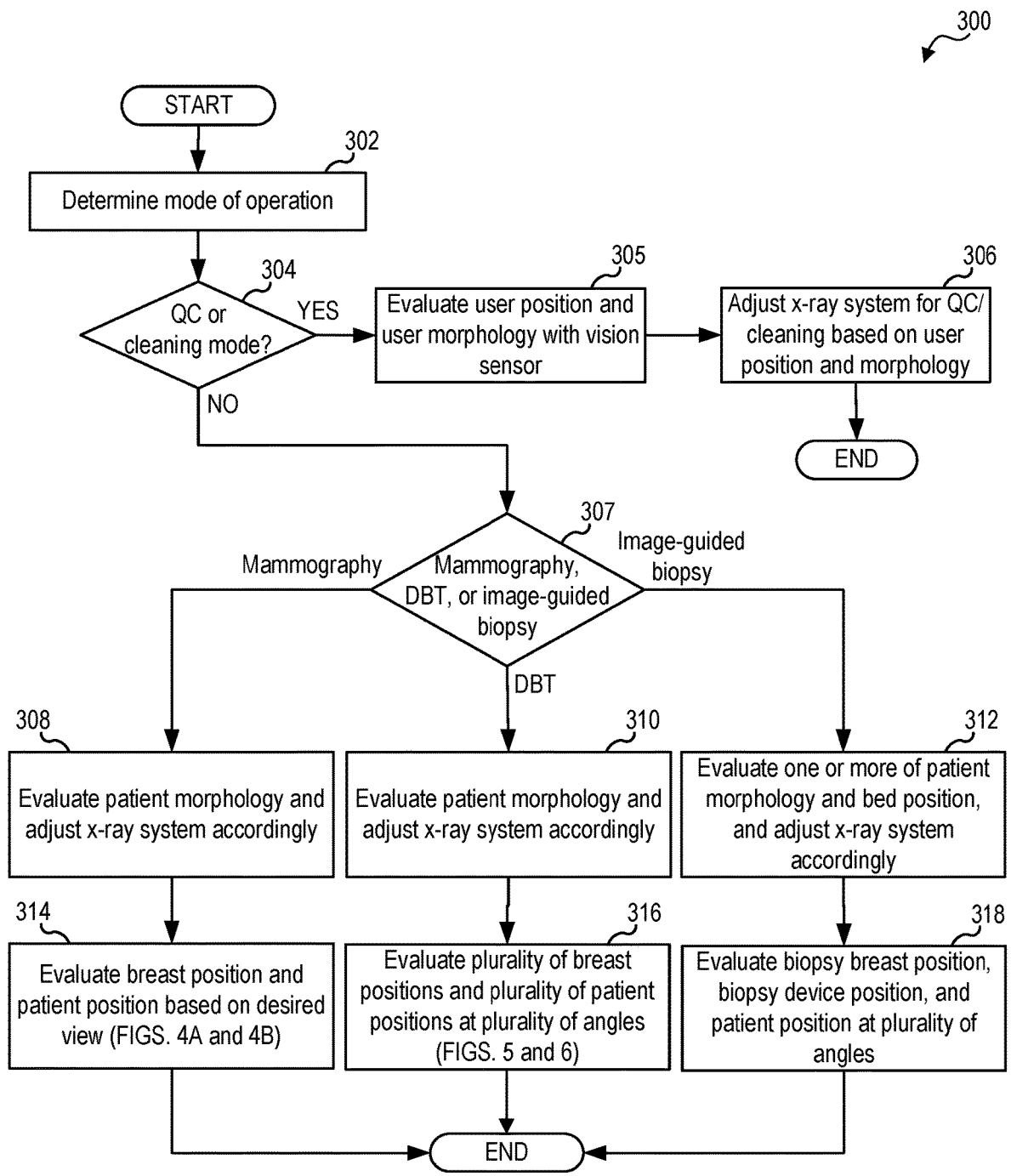
FIG. 3 is a high-level flow chart illustrating a method for evaluating one or more of a breast position, patient position, user position, and user morphology, based on the mode of operation, according to an embodiment of the disclosure.

Turning to FIG. 3, a high-level flow chart illustrating a method 300 for evaluating one or more of a breast position, breast anatomical structures, a patient position, patient morphology, a user position, and user morphology is shown. In particular, the method 300 may be implemented during operation of an imaging system, such as the x-ray system of FIG. 1A, prior to initiating image acquisition in order to evaluate a position of a body part to be imaged with respect to the x-ray imaging system, and a position of the patient with respect to the x-ray system. Method 300 may be implemented by an image processing system, such as controller 44 at FIG. 1A, an edge device connected to the image processing system, a cloud in communication with the image processing system, or any appropriate combination thereof. Method 300 is described with regard to the systems and components of FIG. 1A-1D, although it should be appreciated that method 300 may be implemented with other systems and components without departing from the scope of the present disclosure. Further, the method 300 and other methods herein are described with respect to positioning of a breast and with respect to the x-ray mammography system discussed at FIGS. 1A-1D, however, it will be appreciated that the methods and systems for positioning evaluation (body part and patient) described herein may be implemented with other imaging modalities such as x-ray based imaging modalities including CT, DXA, SPECT, etc., and other modalities such as MM, etc.

Method 300 begins at 302. At 302, the method 300 includes determining the mode of operation of the x-ray imaging system. The mode of operation may be a current mode of operation that a user (that is, a technologist) intends to perform with the x-ray system. In one example, the mode of operation may be determined based on user input. In another example, the vision sensing system may be utilized to determine the mode of operation based on one or more accessories detected by the vision system.

Next, at 304, the method 300 includes confirming if the current mode of operation is any of a quality check (QC) mode and a cleaning mode. If the answer at 304 is YES, the method 300 proceeds to 305. At 305, the method 300 includes evaluating one or more of a user position and a user morphology. The user position includes a location of the user with respect to the x-ray system. The user position may further include a movement of the user from one location to another within a time frame, a pose of the user (e.g., sitting, standing, etc.). The user position may be determined with respect to a reference axis (e.g., vertical axis 60 at FIG. 1A) of the x-ray system, and may be monitored based on input from a first vision sensor, such as the vision sensor 101 at FIG. 1A. The first vision sensor may be a 3-dimensional depth sensing camera, for example. In one embodiment, the vision sensor may not be directly coupled to the x-ray system, and may be positioned (e.g., within a room housing the x-ray system) such that the user and the x-ray system are in a field of view of the vision sensor when the user is within a threshold perimeter of the x-ray system. The threshold perimeter may be based on a size of the examination room in which the x-ray system is located. In another embodiment, the first vision sensor may be coupled to the x-ray system to estimate and monitor user position and morphology. While the present example depicts one vision sensor for user position and user morphology evaluation, it will be appreciated that two or more vision sensors may be utilized. For example, the vision sensor 101 and workstation vision sensor 102 may be utilized to monitor user morphology and position.

The input from the first vision sensor may be usable by a vision sensor data processor to perform tracking of one or more users in the field of view of the vision sensor, and evaluate user position based on the tracking. In one example, the input (e.g., depth information) may be used to perform skeletal tracking, wherein a plurality of joints of the user are identified and analyzed to determine movement, pose, position, etc., of the user. For example, the location of the joints during skeletal tracking may be used to determine the user parameters described above.

The first vision sensor may be used to estimate a user morphology parameter, including a height of the user, in addition to the user's position with respect to the x-ray system. In one example, similar to the determination of user position, the user height may be estimated based on skeletal tracking data. In another example, highest and lowest points of a plurality of point clouds (dataset representing the user) of the user may be utilized to estimate user height. Point clouds may obtained from one or more of 2-dimensional and 3-dimensional images obtained with the vision sensor.

Next, method 300 proceeds to 306. At 306, the method 300 includes adjusting the x-ray system for QC or cleaning based on the user position and morphology. In one example, the controller may adjust one or more features of the x-ray system for cleaning. The one or more features may include a compression paddle holder position on gantry rails, a detector position, a gantry position, and a control station (also referred to herein as workstation) position. The above mentioned features may be adjusted based on the user height to respective cleaning positions for faster and efficient cleaning. That is, the x-ray system may be adapted to suit the user based on user position and user morphology for QC and/or cleaning. As discussed above, based on a camera image of the user from the vision system, the controller may evaluate the user height, and automatically adjust a position of the compression paddle and/or detector based on the user height for QC and/or cleaning. As a result, efficiency of the procedure is improved. Further, the user position may be utilized to determine an order of adjustment. For example, when the user is detected closer to the x-ray system, the gantry position and the compression paddle position may be adjusted for cleaning, while the control station position may be adjusted when the user moves closer to the control station.

If a QC procedure is to be performed, the x-ray system may adapt the one or more features including the compression paddle position, the gantry position, and the workstation position based on user height and position. Upon adjusting one or more features of the x-ray system based on the user position and morphology, the method 300 ends.

Returning to 304, if QC or cleaning mode is not confirmed, the method proceeds to 307. At 307, the method 300 includes confirming if the x-ray system is utilized to perform a mammography, a DBT, or an image-guided biopsy procedure. That is, the method 300 includes determining if a desired mode of operation of the x-ray system is the mammography mode, the DBT mode, or the image-guided biopsy mode.

In one example, the mode of operation of the x-ray system may be determined based on an indication from the user on a user interface of the x-ray system. In one example, the controller may determine the mode of operation based on the user launching an application interface corresponding to the mode of operation. For example, determining the mode of operation based on user indication may include determining an image-guided biopsy mode in response to the user launching an image-guided biopsy interface, determining a DBT mode in response to the user launching a DBT imaging interface, and determining a mammography mode in response to the user launching a mammography interface. It will be appreciated that other modes of user indication, such as user selecting a corresponding icon on the user interface, entering the desired mode on the user interface, etc., may be used for confirming the mode of operation, and are within the scope of the disclosure. Additionally or alternatively to user indication, the mode of operation may be determined based on the vision sensing system detecting the presence of one or more accessories associated with the corresponding procedure. For example, in response to detecting a biopsy device positioned on a detector surface of the x-ray system, the controller may determine that the desired mode of operation is an image-guided biopsy mode. In this case, the application interface for image-guided biopsy may be automatically launched upon detecting the presence of the biopsy device.

If the desired mode of operation is the mammography mode, the method 300 proceeds to 308. At 308, the method 300 includes evaluating a patient morphology, and adjusting the x-ray system based on the patient morphology. The patient morphology may include a patient size, the patient size including one or more of a patient height, a patient weight, and a patient body mass index. In one example, the patient size may be determined based on a user indication via the user interface. In another example, the patient size may be estimated by utilizing the second vision sensor. Adjusting the x-ray system based on the patient morphology may include adjusting one or more of a gantry position (e.g., lift of the gantry may be adjusted based on the patient height), and a collimation for the x-rays based on the patient morphology (e.g., a collimation plate may be controlled to match the area of the breast).

Upon adjusting the x-ray system, the method 300 proceeds to 314. At 314, the method 300 includes evaluating a breast position based on one or more breast anatomical structures with a second vision sensor, and a patient position for one or more mammography views with the first vision sensor. The details of evaluating breast position and the patient position for mammography views will be discussed at FIGS. 4A and 4B.

If the desired mode of operation is the DBT mode, the method 300 proceeds to 310 to evaluate patient morphology and adjust the x-ray system based on the evaluation. Step 310 is similar to 308, and will not be repeated.

Next, the method 300 proceeds to 316. At 316, the method 300 includes evaluating a plurality of breast positions based the one or more breast anatomical structures with the second vision sensor and a plurality of patient positions with the first vision sensor at a plurality of angles within the angular range for tomosynthesis. The details of evaluating the plurality of breast positions and the plurality of patient positions are discussed at FIGS. 5 and 6. Briefly, before beginning x-ray image acquisition, the breast and patient position are evaluated by moving the gantry to a few angulations that correspond to x-ray source positions during DBT acquisition, and ensuring with the RGB-D camera that the breast is positioned as desired. For example, while patient's belly or shoulder or contralateral breast may not be visible in the first initial DBT position, at a different DBT angulation, these extra structures may be visible. Therefore, during DBT, breast position and/or patient position is evaluated at more than one x-ray tube angulation.

If the desired mode of operation is the image-guided biopsy mode, the method proceeds to 312. At 312, the method 300 includes evaluating the patient morphology, and adjusting one or more of a bed position and the x-ray system based on the patient morphology. The patient morphology may include a patient size, the patient size including one or more of a patient height, a patient weight, and a patient body mass index, which may be determined and/or estimated as discussed above at 308. Further, a biopsy bed position may be adjusted (via a biopsy bed actuator, for example) to adjust one or more of a biopsy bed height and inclination based on the patient morphology. Further, adjusting the x-ray system based on the patient morphology may include adjusting one or more of a gantry position, and a collimation for the x-rays based on the patient morphology.] In this way, prior to evaluating one or more of patient position and breast position, a patient morphology may be evaluated and the x-ray system may be adjusted to automatically set up the x-ray system for the patient.

318. At 318, the method 300 includes evaluating a biopsy breast position based on one or more anatomical structures of the breast with the second vision sensor, a biopsy device position with the second vision sensor, and a patient position for biopsy with the first vision sensor. The evaluation of biopsy breast position may be based on the type of imaging used to guide the biopsy. For example, if DBT-guided biopsy is performed, the evaluation of biopsy breast position and patient body position may be similar to the positioning evaluation and feedback for DBT, as discussed below at FIGS. 5 and 6. In addition to breast position and patient body positioning, biopsy device position may be evaluated, and real-time feedback may be provided to reduce imaging artifacts due to metallic object associated with the biopsy device.

Figure 4A:
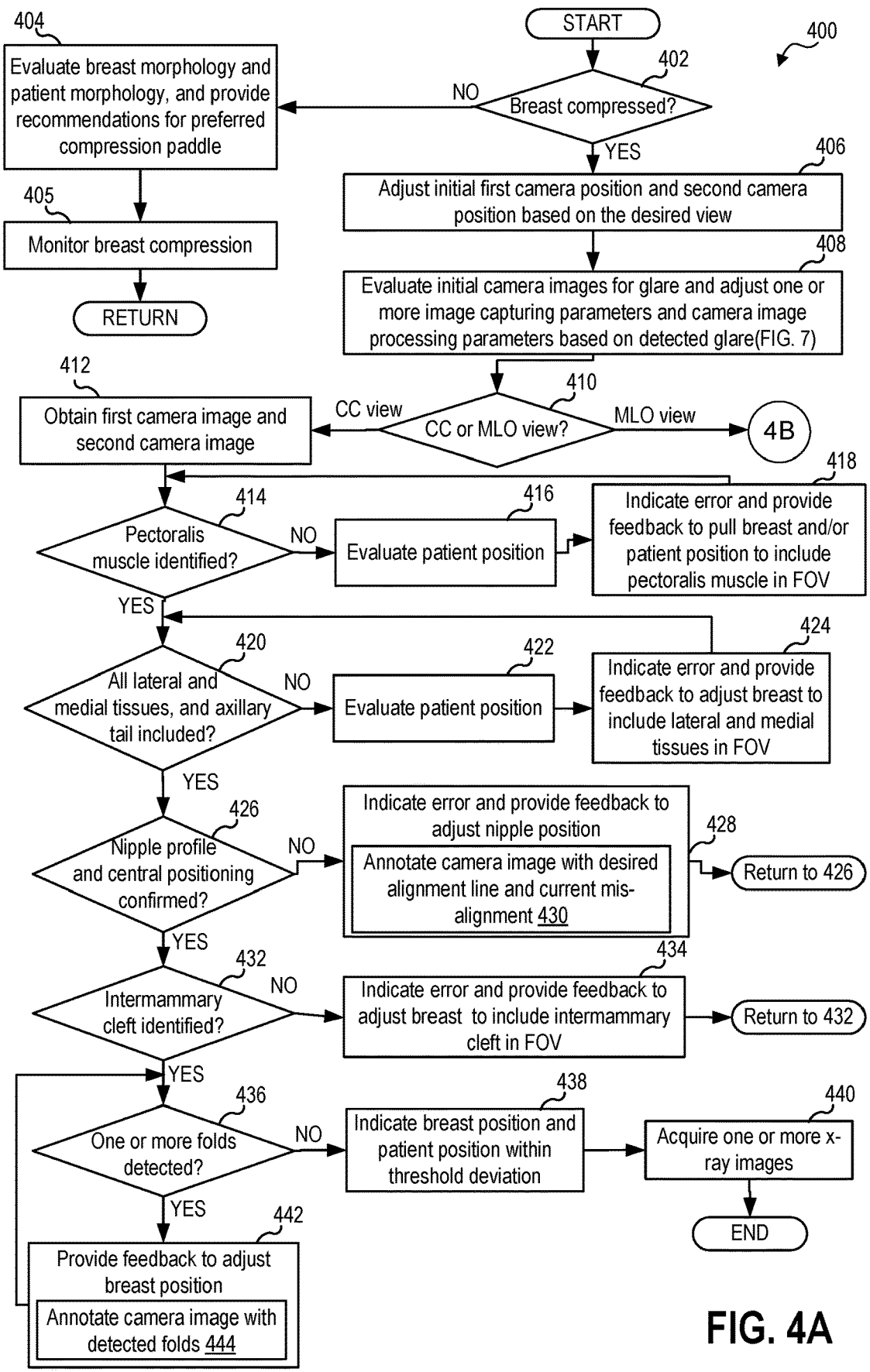
FIG. 4A is a high-level flow chart illustrating a method for evaluating breast position and patient position during mammography and providing real-time feedback for adjusting breast position and patient position for improving mammography image quality, according to an embodiment of the disclosure.

Turning to FIG. 4A, a high-level flow chart illustrating a method 400 for evaluating one or more of a breast position and a patient position, and providing real-time feedback to the user to obtain a desired breast position for mammography is shown. Specifically, the method 400 may be performed prior to initiating x-ray image acquisition in order to endure that the desired breast position is achieved. The breast position evaluation may be performed based on input from a second vision sensor, such as the second vision sensor 154 at FIG. 1B, and the patient position evaluation may be performed based on input from one or more of the second vision sensor and a first vision sensor, such as camera at FIG. 1A. In some examples, the second vision sensor may also be used to capture partial portions of the patient (e.g., patient shoulder) and thus, provide a partial view of the patient in addition to views of compressed breast. The method 400 may be implemented by an image processing system, such as controller 44 at FIG. 1A, an edge device connected to the image processing system, a cloud in communication with the image processing system, or any appropriate combination thereof. Method 400 is described with regard to the systems and components of FIGS. 1A-1D, although it should be appreciated that method 400 may be implemented with other systems and components without departing from the scope of the present disclosure. Further, real time feed-back may be provided via a display portion of a user interface coupled to the x-ray mammography system and positioned near the x-ray mammography system such that the user can view the real-time feedback and the images displayed on the user interface, while making necessary breast, patient, and x-ray system adjustments to obtain the desired breast positioning for acquisition. An exemplary user interface positioned close to the x-ray system is shown at FIGS. 1B and 1C at user interface 195, and real-time feedback and images may be displayed on the display portion 196 of the user interface 195. Additionally, real-time feedback and the images may also be displayed at the workstation user interface 50 via the display portion 50.

Further, it will be appreciated that the systems and methods described herein may allow the user to take necessary action when desired. For example, in some examples, if the user would like to proceed image acquisition with a current position, even though the real-time feedback may indicate additional adjustments, an option may be provided, via the user interface for example, for the user to initiate image acquisition with the current position.

The method 400 begins at 402. At 402, the method 400 includes confirming if a breast to be imaged is compressed between a compression paddle, such as the compression paddle 164 at FIG. 1B, and a detector, such as the detector 168 at FIG. 1B. In one example, breast compression may be determined based on compression feedback from one or more of a force sensor and a pressure sensor coupled to the compression paddle. In another example, breast compression may be determined based on the user confirmation of compression via the user interface. In yet another example, in addition to or alternative to user confirmation, breast compression may be determined based on a final (locked) position of the compression paddle. The compression paddle position may be determined based on input from one or more of the first and the second vision sensors, for example. The final compression paddle position may indicate that the breast is compressed for subsequent positioning evaluation and later on, x-ray mammography imaging. If breast compression is confirmed, the answer at 402 is YES, and the method 400 proceeds to 406.

If breast compression is not confirmed, the answer at 402 is NO, and the method 400 proceeds to 404. At 404, the method 400 includes evaluating breast morphology and patient morphology based on input from one or more of the first and the second vision sensors. The evaluation of breast morphology and patient morphology may be performed to identify one or more preferred compression paddle types based on the breast and patient morphology and the type of imaging procedure to be performed before initiating compression. Accordingly, evaluating breast morphology may include estimating a breast size of the patient, which may include a breast thickness, and evaluating patient morphology may include estimating a patient height. In one example, different views of the patient, such as a front view and a side view of the patient, may be obtained from the first and the second vision sensors, and camera images of the different views may be utilized by the imaging processor for estimating the breast size and the patient height. The breast size, the patient height, and the imaging mode may be utilized by the imaging processor to indicate to the user, via the user interface, such as user interface 195 at FIGS. 1B and 1C, one or more preferred compression paddles for the desired imaging mode and patient.

Further, in some embodiments, prior to initiating compression, based on the patient morphology and the desired view (e.g., CC view or MLO view for mammography), real-time guidance for initial positioning the patient with respect to the x-ray system, such as sitting, standing, reclined, etc., may be provided to the user. The real time guidance may a voice feedback, and/or via indications on the user interface.

Continuing on to 405, the method 400 may monitor for breast compression. The method 400 then returns.

Returning to 406, upon confirmation of breast compression, the method 400 includes adjusting the first vision sensor position, wherein the first vision sensor used for patient position evaluation, and the second vision sensor position, wherein the second vision sensor is used for one or more of breast position evaluation and patient position evaluation, based on the desired view for mammography.

In one example, the first vision sensor position may be adjusted so that a field of view of the first vision sensor includes a whole body of the patient, the compressed breast, and the x-ray imaging system. In another example, the first vision sensor position may be adjusted so that an upper body portion of the patient (e.g., from the top of the head up to the waist), the compressed breast, and a portion of the x-ray system, including the imaging volume (the imaging volume comprising the compression paddle, the breast, and the detector), the gantry, and a portion of the support column, are in the field of view of the first vision sensor. Further, in other examples, additionally, the first vision sensor position may be adjusted to obtain a view for measuring a distance between the support column and the patient's shoulder along a horizontal imaging plane (e.g. parallel to the detector surface). The view may be a side view of the patient body and the x-ray imaging system, for example. Furthermore, it will be appreciated that the first vision sensor position may be based on the position of the patient (sitting, standing, or reclined).

The second vision sensor may be positioned to obtain a field of view of the x-ray beam generated from the x-ray source. The second vision sensor is positioned on the gantry, and as such, in one example, the gantry may be adjusted based on the mammography desired view so that the second vision sensor captures images consistent with the desired view. For example, if the desired view is a cranio-caudal (CC) view, the second camera and the gantry may be adjusted such that the x-ray source is at a medial position (wherein a vertical axis of the x-ray source, such as the vertical axis 60, is perpendicular to the detection surface) with respect to the detector, and a vertical axis of the second vision sensor is perpendicular to the detection surface such that the second vision sensor captures the CC view of the compressed breast. Further, the second vision sensor position may be adjusted such that the x-ray field of view is within the camera field of view. In one example, an angle of view of the second vision sensor may be greater than a cone angle of the x-ray source. An example positioning of the x-ray source and the second vision sensor for CC view evaluation is illustrated at FIG. 8A.

Turning to FIG. 8A, a portion 800 of an x-ray system, such as the x-ray system 10 at FIG. 1A, is shown. Many of the elements of FIG. 8A correspond to similarly numbered elements already described above for FIGS. 1A-1D; such elements will not be described again for the sake of brevity. The portion 800 shows an x-ray source 802 of the x-ray system at the medial position for CC view where the vertical axis 60 is perpendicular to detector 168, the second vision sensor 154 with its vertical axis (not shown) also perpendicular to the detector 168, and a compressed breast 811 positioned between the detector 168 and compression paddle 164. The breast position may be evaluated prior to initiating the x-ray mammography scan. Accordingly, the vision sensor 154 may be adjusted such that an angle of view $\alpha 2$ of the vision sensor includes the compressed breast 811 and is greater than a cone angle $\alpha 1$ of a cone beam 812 of the x-ray source 802. Further, a camera field of view 816 (including a horizontal field of view and a vertical field of view) of the vision sensor 154 may be greater than a projection field of view 814 of the detector.

Returning to step 406 at FIG. 4A, if the desired view is a mediolateral oblique (MLO) view, the gantry may be adjusted such that the x-ray source is at an angle (e.g., 45 degrees) with respect to the medial position, and the vertical axis of the second vision sensor is also at the same angle with respect to the medial position such that the second vision sensor captures the MLO view of the compressed breast prior to initiating the x-ray mammography scan. Further, for the MLO view, the camera position may be as the camera position discussed for CC view, wherein the x-ray field of view is within the camera field of view. In one example, an angle of view of the second vision sensor may be greater than a cone angle of the x-ray source. An example positioning of the x-ray source and the second vision sensor for MLO view evaluation is illustrated at FIG. 8B.

Turning to FIG. 8B, a portion 850 of an x-ray system, such as the x-ray system 10 at FIG. 1A, is shown. Many of the elements of FIG. 8B correspond to similarly numbered elements already described above for FIGS. 1A-1C; such elements will not be described again for the sake of brevity. The portion 850 shows an x-ray source 802 of the x-ray system positioned for MLO view at an angle 45 degrees with respect to the vertical axis 60, the second vision sensor 154 with its vertical axis 860 also at 45 degrees with respect to the vertical axis 60, and a compressed breast 811 positioned between the detector 168 and compression paddle 164. The breast position may be evaluated prior to initiating the x-ray mammography scan. Accordingly, the vision sensor 154 may be adjusted such that an angle of view $\alpha 2$ of the vision sensor includes the compressed breast 811 and is greater than a cone angle $\alpha 1$ of a cone beam 812 of the x-ray source 802. Further, a camera field of view 822 (including a horizontal field of view and a vertical field of view) of the vision sensor 154 may be greater than a projection field of view 820 of the detector.

Returning to step 406 at FIG. 4A, upon adjusting the first camera position and the second camera position based on the desired view (CC view or MLO view), the method 400 proceeds to 408. At 408, the method 400 includes evaluating initial camera images for glare. For example, examination room light and camera lens may generate glare on camera images, which may degrade subsequent evaluation of the breast position. As such, after positioning the camera for the desired view, one or more initial camera images may be obtained, and evaluated for glare. Depending on an amount of glare and location of the glare, one or more camera image capturing parameters including camera position, lighting, and polarization, and camera image processing parameters may be adjusted to reduce glare. An exemplary method for evaluating glare and performing glare reduction adjustments is described at FIG. 7.

Continuing on to 410, the method 400 includes determining if the desired view is CC view or MLO view. The desired view may be determined based on user indication, for example.

If the desired view if the CC view, the method 400 proceeds to 412. At 412, the method 400 includes obtaining a first camera image from the first vision sensor, and a second camera image from the second vision sensor. In one example, the first camera image and the second camera image may be utilized as input into an artificial intelligence based deep-learning model for evaluation of compressed breast position and patient position in the CC view. In another example, additionally or alternatively, one or more image processing algorithms and segmentation algorithms that are not based on artificial intelligence, such as mathematical morphology, active contours algorithms, etc., may be used.

Next, at 414, the method 400 includes determining if pectoralis muscle of the compressed breast is identified in the second camera image. Specifically, the method 400 may determine if the pectoralis muscle is included within the compressed breast between the detector and the compression paddle. In one example, the second camera image may include a RGB image and a depth image. The pectoralis muscle may be identified based on segmentation of one or more of the RGB image and the depth image. For example, pectoralis muscle zone may be detected using Mask Region—Convolutional Neural Network (Mask R-CNN) deep learning algorithms.

If the pectoralis muscle is not identified, the answer at 414 is NO, and the method 400 proceeds to 416. At 416, the method includes evaluating patient position based on input from the first camera. Evaluating patient position includes evaluating a patient shoulder distance from the x-ray system, a patient head position, a patient feet position, a patient posture, a body rotation, and a patient spine position. In evaluating the patient shoulder distance, a distance of a patient's shoulder corresponding to the ipsilateral side of the breast that is imaged from a vertical edge of a support column, such as support column 170 at FIGS. 1B and 1C, may be determined. That is, if the right breast is imaged, the right shoulder distance from the corresponding vertical side edge of the support column may be determined, and if the left breast is imaged, the left shoulder distance from the corresponding vertical side edge of the support column may be determined. If the patient shoulder distance is greater than a threshold shoulder distance, it may be determined that the patient is not sufficiently close to the x-ray system. If the patient shoulder distance is less than the threshold shoulder distance, it may be determined that the patient is sufficiently close to the x-ray system for sufficient breast tissue inclusion, and thus, patient position as to shoulder distance need not be adjusted.

Further, based on the first camera image of the patient and the x-ray system, a level of shoulder drooping may be evaluated. In order to include a greater amount of breast tissue, and reduce tightening of the pectoralis muscles, the shoulders may be drooping, and as such, the controller may evaluate a shoulder-to-ear distance of the patient to ensure that the shoulder is not elevated. Accordingly, the controller may determine if the shoulder-to-ear distance between the patient's shoulder and ipsilateral ear is greater than a threshold, the threshold based on patient morphology. Accordingly, a distance between the patient's shoulder and the ipsilateral ear may be determined to evaluate the level of droop, wherein the level of droop is greater for greater distance from between the ear and shoulder.

Upon evaluating the patient position, the method 400 proceeds to 418. At 418, the method 400 includes indicating to the user, via the user interface, that the pectoralis muscle is not pulled in and the patient position (based on the evaluation at 416). In particular, if patient shoulder distance is greater than the threshold, the controller may indicate that the patient is father away from the x-ray system than desired. Accordingly, a real-time feedback may be provided to the user to adjust the patient position and the breast position to move the patient closer to the x-ray system, and include more breast tissue for compression so that pectoralis muscle is included.

If the patient position indicates that the patient shoulder distance is within the threshold distance, at the next step (that is, at 418) the method 400 includes indicating to the user, via the user interface, that the pectoralis muscle is not visible but the patient is within the threshold distance from the support structure. Further, the real-time feedback may include an indication to pull additional breast tissue for compression without moving the patient farther away from the vertical column.

Additionally, if the shoulder-to-ear distance is greater than threshold, the method 400 includes indicating (at 418) that the patient is at the desired drooping position, and no further shoulder adjustment is required. Accordingly, the real-time feedback may include an indication to pull additional breast tissue with reduced patient body movement. However, if the shoulder-to-ear distance is less than the threshold, the method 400 includes indicating that the patient's shoulder is elevated, and may include providing feedback to adjust patient position such that the shoulders droop to the desired level and pulling additional breast tissue for compression.

In this way, real-time feedback is provided to the user based on anatomical landmarks of the compressed breast identified from the compressed breast image from the second camera and patient position with respect to x-ray system and patient posture from the first camera image.

In one exemplary embodiment, if the shoulder distance and the shoulder-to-ear distance meet their respective criteria, then one or more additional patient position parameters, including one or more of patient feet position, the patient body rotation (slightly turned medially), and a patient spine position (leaning towards the x-ray system from the waist) may be evaluated, and feedback may be provided accordingly to adjust the patient position. For example, it may be determined if the patient's feet are pointing towards the x-ray system. If not, the real-time feedback to adjust patient feet to point towards the x-ray system may be provided.

In one example, the real-time feedback may include a voice feedback in combination with one or more indications on the user interface. The indications may include graphical indications for desired position and orientations overlaid on the camera images in order to assist the user in achieving proper patient position.

Upon providing real-time feedback to the user, the method 400 may continue to acquire first and second camera images, and may return to 414 evaluate if pectoralis muscle is included after adjustment. It will be appreciated that after each feedback, and corresponding breast and/or patient position adjustment by the user, the first and second vision sensors may acquire new camera images, which are then input into the AI model for further subsequent breast and patient position evaluation. Thus, after real time feedback at steps 418, 424, 428, and 442, prior to evaluating next breast and patient positions, new camera images from the first and the second vision sensor may be acquired for subsequent analysis.

Returning to 414, if the pectoralis muscle is identified, the answer at 414 is YES, and the method 400 proceeds to 420. At 420, the method 400 includes evaluating if lateral and medial tissues are included in the compressed breast tissue. In particular, evaluating inclusion of medial tissues includes determining if medial border is well defined, which may be based on visualization of cleavage, for example. Evaluation of inclusion of lateral tissues further includes determining if lateral aspects, including lateral border, are well defined.

If lateral and medial tissues are not included, the answer at 420 is NO, and the method 400 proceeds to 422. At 422, the method 400 includes evaluating patient position based on input from the first camera. Specifically, the patient position may be evaluated for patient position parameters that may increase inclusion of the medial and lateral tissues. The patient position parameters for medial and lateral tissue inclusion includes one or more of the head position of the patient, and shoulder position of the patient. In order to include adequate medial tissue, the patient's head may be turned towards the contralateral side. However, if the head is tilted, sufficient medial tissue may not be included. Accordingly, a level of tilt of the head towards the contralateral side may be determined and further, it may be determined if the head is turned towards the contralateral side based on head position and shoulder position.

Further, in some examples, in order to increase inclusion of the medial tissues, the contralateral breast position of the patient may be evaluated.

Additionally, in some examples, a gantry position, may be evaluated (with the first camera, for example), and real-time feedback may be provided. For example, the gantry can be adjusted to include the correct tissue in the FOV. The gantry may be at a certain position from the inframammary fold of the patient to get the required tissue.

Upon evaluating the patient position for inclusion of medial and lateral tissues, the method 400 proceeds to 424. At 424, the method 400 includes indicating that all lateral and medial tissues are not included. Further, the evaluation of patient position may be indicated and feedback may be provided based on the patient position evaluation. In one example, if the level of tilt is less than a tilt threshold, and if the head is turned towards the contralateral side, the controller may indicate that the head position is at a desired position for medial and lateral tissue inclusion, and may provide real-time feedback to pull more breast tissue for inclusion of medial and lateral tissues. If the patient position indicates that the level of tilt is greater than the tilt threshold, the controller may indicate that the head is tilted, and may indicate to the user to reposition the head to turn the patient's head to the contralateral side (that is, side opposite to the side of the breast being compressed).

As discussed above, the real-time feedback may include a voice feedback in combination with one or more indications on the user interface. The indications may include graphical indications for desired position and orientations overlaid on the camera images in order to assist the user in achieving proper patient position.

Further, the method 400 may include determining if axillary tissues are included. The inclusion of axillary tissues may be based on a contour of the compressed breast outline, and axillary tail outline. The axillary tail shall be located above the detector. Axillary tail may be detected by deep learning methods like mask R-CNN methods or by image processing (e.g., pattern matching).

In this way, the breast position and the patient position may be evaluated for inclusion of medial and lateral tissues, and axillary tissues after confirming desired inclusion of pectoralis muscles, and real-time feedback, based on the camera images acquired by the first and the second sensor, may be provided to the user to improve breast positioning for the desired mammographic view.

Upon providing feedback for lateral and medial tissue inclusion, the method 400 returns to 420 to continue evaluation for medial and lateral tissue inclusion.

At 420, if the medial and lateral tissue inclusion is confirmed, the answer at 420 is YES, and the method proceeds to 426. At 426, the method 400 includes determining if the nipple is in profile for the CC view. In particular, the nipple profile must be visible, and further, the nipple may be positioned centrally and should not be pointing medially or laterally. The nipple position may be evaluated using shape and color descriptors based on one or more camera images from the second vision sensor.

If the nipple is not in profile or not pointing centrally, the answer at 426 is NO, and the method 400 proceeds to 428. At 428, the method 400 includes indicating to the user that the nipple is not in profile or not pointing centrally, based on the nipple position evaluation. Further, one or more feedbacks to adjust nipple position may be provided. The feedback includes, annotating the camera image from the second vision sensor with an alignment line, the alignment line indicating the central line along which the nipple should be positioned. Further, a current mis-alignment may be indicated, with an arrow for example.

Further, at 426, the method 400 may include determining if the compressed breast is centrally positioned on the detector, and if a left portion of the breast and a right portion of the breast are symmetrical (also referred to herein as left-right symmetry). This may include determining a nipple to detector edge line position on the camera image, and determining of the left portion to the left of the nipple to detector line and the right portion to the right of the nipple to detector line show symmetry within threshold limits with respect to one or more of shape, area, and volume. Further, a real-time feedback to centrally position the breast and obtain the left-right symmetry may be provided. This includes an annotation of central region (or a rectangular box) within which the compressed breast is present when central position is achieved may be shown on the camera images, and a direction to pull/adjust the breast to obtain acceptable left-right symmetry may be indicated on the camera image.

If nipple is in profile and at the central position, the answer at 426 is YES, and the method 400 proceeds to 432. At 432, the method 400 includes confirming if the intermammary cleft is visible. Visibility of intermammary cleft may be determined based on segmentation of one or more of the RGB image and the depth image. In another example, visibility of intermammary cleft may be detected based on the camera images using a CNN algorithm, such as a Mask R-CNN deep learning algorithms. If the inframammary fold is not visible, the method 400 proceeds to 434. At 434, the method 400 includes indicating, via the user interface, that the intermammary cleft is not visible, and providing feedback to adjust breast tissue to include the intermammary cleft in the compressed breast volume. The indication may be a graphical indication, such as an arrow pointing to where the intermammary cleft is expected to be visible. Further, the indication may include highlighting, on the camera image, specific regions of the breast to be adjusted so as to include the intermammary cleft. Furthermore, a direction of breast movement for adjustment may be indicated. For example, graphical indications, such as arrows, may be used to indicate to the user the direction to pull the breast. In some embodiments, additionally, undesired movements, such as rotation of the breast, may also be presented to the user with an indication to not perform the undesired movement. Furthermore, one or more indications as to maintain current patient position may be provided. In some embodiments, the indications may be animated. In addition to the graphical indications discussed above, voice feedback may be provided to guide to user to position the breast. The method 400 then returns to monitor for inclusion of intermammary cleft.

If the intermammary cleft is visible, the answer at 432 is YES, the method 400 proceeds to 436. At 436, the method 400 includes confirming if one or more folds are detected. The one or more folds may include one or more of skin wrinkles and skin folds on the breast under compression. In particular, the method 400 may determine if one or more skin folds are detected in one or more of a caudal area, lateral area, and medial area of the compressed breast. The skin wrinkles and/or folds may cause imaging artifacts or obscure nearby anatomical structures during x-ray imaging. As such, if one or more folds are detected, the answer at 436 is YES, and the method 400 proceeds to 442. At 442, the method 400 includes indicating to the user that one or more folds are visible, and further includes annotating the camera image to show the one or more folds, via graphical indications, for example. Further, feedback regarding the desired adjustment to reduce the one or more folds may be provided. As an example, a voice feedback and/or an indication on the user interface to smooth the one or more folds by pulling the skin towards the nipple. Furthermore, additionally, a direction of undesired movement, pulling the skin upwards posteriorly, may be indicated to the user with an indication to avoid the undesired movement. The method 400 then returns to 436 to monitor the one or more folds.

At 436, if one or more skin folds/wrinkles are not detected, the method 400 proceeds to 438. At 438, the method 400 includes indicating to the user, via the user interface, that the breast position and the patient position are confirmed for x-ray acquisition. Continuing on to 440, the method 400 includes acquiring one or more x-ray projection images of the CC view of the compressed breast. The method 400, then ends.

In this way, one vision sensor may be utilized to evaluate breast position and provide real-time feedback to obtain the desired breast positioning for CC view; and another vision sensor may be utilized to evaluate patient position and provide real-time feedback to adjust the patient position so that the desired breast position for CC view may be achieved. As a result, breast position and patient position may be adjusted based on input from the two vision sensors to obtain consistent and high quality mammograms.

While the above method describes evaluating the breast position and patient position, in some embodiments, the breast position may be evaluated with the second camera independent of the patient position, and are within the scope of the disclosure. For example, evaluating breast position based on camera images from the second camera for the CC view may include pectoralis evaluation, lateral and medial tissue evaluation, nipple position evaluation, and one or more skin folds and wrinkles evaluation. Further, real-time feedback may be provided based on the breast position evaluation. The real-time feedback may include one or more breast position adjustments and patient position adjustments.

In other embodiments, the patient position may be monitored/evaluated independent of the breast position evaluation. In one example, breast position may be evaluated and upon confirmation of desired breast position, the patient position may be evaluated with one or more of the first camera and the second camera, and real-time feedback may be provided to obtain a desired patient position prior to initiating image acquisition. In another example, patient position alone may be evaluated and real-time feedback may be provided to obtain the desired patient position prior to initiating the image acquisition.

Further, in some examples, the second camera that is utilized for breast position monitoring may be utilized to evaluate patient position. For example, images from the second camera may be analyzed to check if irrelevant structures, such as contralateral breast, patient belly, etc., are not visible in the field of view of the second camera, and thus not visible in the field of view of the x-ray source. As a result, irrelevant structures that may obstruct visualization of the compressed breast tissue may be reduced.

Further, it will be appreciated the order of evaluation, wherein the pectoral muscles are evaluated first, followed by medial and lateral tissues, nipple profile, and IMF, and finally, the folds are evaluated, allows for efficient and faster evaluation and feed-back.

Furthermore, one or more of breast position and patient position evaluation may be performed and real-time feedback may be provided for other views including but not limited to mediolateral view (ML view), lateromedial view (LM view), lateromedial oblique view (LMO), late mediolateral view, step oblique views, spot compression view, double spot compression view, axillary view, cleavage view, tangential view, reversed CC view, rolled CC view, bulls eye CC view, elevated craniocaudal projection, caudal cranial projection, oblique projection, and inferomedial superolateral oblique projection.

Figure 4B:
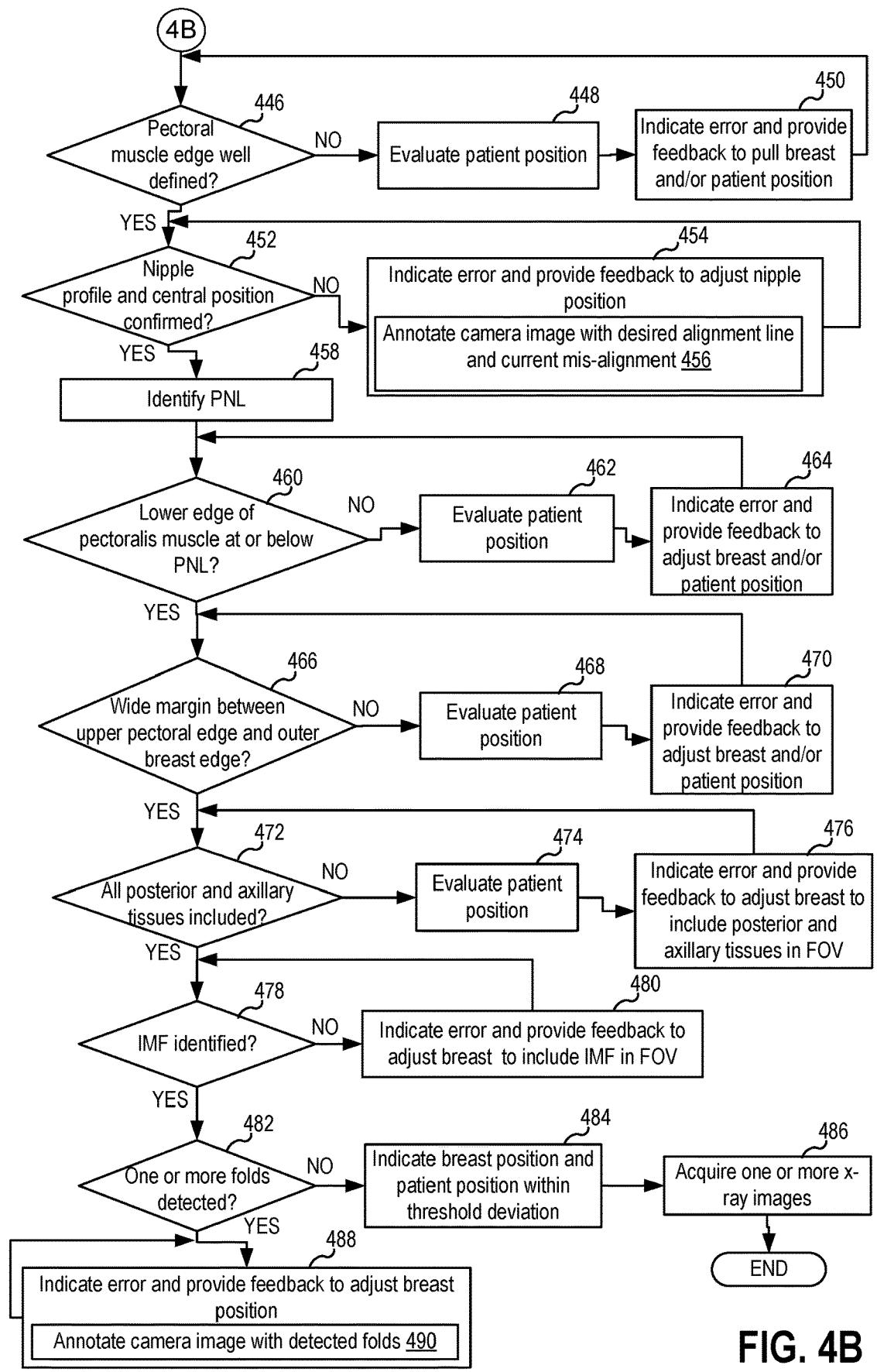
FIG. 4B is a continuation of FIG. 4A.

Returning to 410, if the desired view if the MLO view, the method 400 proceeds to 446 at FIG. 4B. At 446, the method 400 includes determining if the pectoral muscle edge is well defined based on the camera image of the compressed breast acquired with the second vision sensor. In one example, evaluating pectoral muscle in MLO view may include evaluating one or more of axillary position, a breast border angle, and curvature. For detection of breast shape, classical camera image segmentation methods may be utilized. In another example, a convolutional neural network (CNN) may be trained based on X-ray images and corresponding camera (RGB-D) images. For example, on an x-ray image if one or more breast position evaluation parameters (e.g., pectoral muscle edge) are positioned as desired, then the corresponding camera image may be determined to show the desired compressed breast position for the one or more breast position evaluation parameters. Thus, a plurality of camera images that show desired compressed position may be identified based on the corresponding x-ray images showing the desired breast position parameters, and the CNN may be trained on the plurality of camera images identified. The inference on pectoral placement may then be performed with the trained network during breast position evaluation. If the pectoral muscle edge is not identified, and/or an edge shape is not consistent with a desired edge shape (e.g., a convex shape or straight line), the answer at 446 is NO, and the method 400 proceeds to 448.

In some embodiments, the pectoral muscle placement (that is, the pectoral muscle edge) may be evaluated after x-ray image acquisition. In one example, if a confidence level of detection of pectoral muscle edge definition on the RGB images is less than a threshold confidence, the pectoral muscle edge definition may be evaluated after x-ray image acquisition on the x-ray images.

At 448, the method 400 includes evaluating patient position. The patient position may be evaluated based on input from the first vision sensor. Specifically, the patient position with respect to the x-ray system may be evaluated. This includes a patient ipsilateral arm position with respect to the detector, a patient hip and shoulder position with respect to the x-ray system, and a position of the compression paddle with respect to the patient. For example, the controller may evaluate if a corner of the detector touching the upper arm of the patient is positioned posterior to the ipsilateral arm pit, the patient's hip is within a desired distance from a lower corner of the image receptor and positioned anteriorly, the patient's hips and shoulders are facing the x-ray unit, and an upper edge of the compression paddle at a desired angle from the clavicle. Continuing on to 450, the method 400 includes providing feedback to the user to adjust one or more of breast position and patient position. For example, if one or more of the above-mentioned patient position parameters are not confirmed, the inconsistencies may be indicated to the user, via the user interface, and real-time feedback may be provided to adjust the inconsistent patient position. Further, the real-time feedback may include instructions to pull the breast upwards and outward before resting on the detector surface to ensure inclusion of the pectoral muscle wall. The method 400 then returns to 446.

It will be appreciated that after each feedback, and corresponding breast and/or patient position adjustment by the user, the first and second vision sensors may acquire new camera images, which are then input into the AI model for further subsequent breast and patient position evaluation. Thus, after real time feedback at steps 448, 454, 464, 470, 476, 480, and 484, prior to evaluating next breast and patient positions, new camera images from the first and the second vision sensor may be acquired for subsequent analysis.

At 446, if the pectoral muscle edge is identified, and an edge shape is consistent with a desired edge shape, the answer at 446 is YES, and the method 400 proceeds to 452.

At 452, the method 400 includes confirming if the nipple is in profile. The nipple profile confirmation may be based on position of the nipple and visibility of the nipple profile in the camera image. Further, at 452, the method 400 may include determining if the compressed breast is centrally positioned on the detector, and if a left portion of the breast and a right portion of the breast are symmetrical. The determination of central position and left-right symmetry may be performed as discussed at 426. If the nipple is not in profile, the compressed breast is not centrally positioned, and/or left-right symmetry is not within the threshold limits (with regards to shape, area and/or volume, for example), the answer at 452 is NO, and the method 400 proceeds to 454.

At 454, the method 400 includes indicating to the user that the nipple is not in profile, the compressed breast is not centrally positioned, and/or left-right symmetry is not within the threshold limits and further includes providing feedback to adjust the breast position to bring the nipple in profile, position the breast centrally, and obtain acceptable left-right symmetry. The feedback includes, at 456, annotating the camera image from the second vision sensor with an alignment line for the MLO view, the alignment line indicating the central line along which the nipple should be positioned. Further, a current mis-alignment may be indicated, with an arrow for example. Further, an annotation of central region (or a rectangular box) within which the compressed breast is present when central position is achieved may be shown on the camera images. Furthermore, a direction to pull/adjust the breast to obtain acceptable left-right symmetry may be indicated on the camera image.

Further, in the MLO view, the method 400 may evaluate an amount of sagging of the compressed breast. That is, based on the camera images, the method may determine the compressed breast is bulging downward, and if so, the method 40o may provide additional feedback to reduce sagging. The method then returns to 452.

If the nipple is in profile, the answer at 452 is YES, and the method 400 proceeds to 458. At 458, the method 400 includes identifying a pectoralis-nipple line (PNL). The PNL may be identified based on the position of the nipple and the pectoral edge.

Next, at 460, the method 400 includes inferring if a lower edge of pectoralis muscle is at or below the PNL. If the answer at 460 is NO, the method 400 proceeds to 462. At 462, the method includes evaluating patient position. The evaluation of patient position may be similar to the position evaluation at 448, and will not be repeated for brevity. Continuing on to 448, the method 400 includes indicating to the user, via the user interface, that the lower edge of pectoralis muscle is not at or below the PNL, and may provide real-time feedback to adjust one or more of breast position and patient position to move the lower edge at or below the PNL. The method 400 then returns to 460.

If the lower edge is at or below the PNL, the answer at 460 is YES, and the method 400 proceeds to 466. At 466, the method 400 includes inferring if there is a wide margin between an upper pectoral edge and an upper outer breast edge. Accordingly, in one example, it may be determined if an area of a region between the upper pectoral edge and the upper outer breast edge is greater than a threshold area. If wide margin is not confirmed, the answer at 466 is NO, and the method 400 proceeds to 468 to evaluate patient position as discussed above at 448. Upon evaluating the patient position, the method 400 proceeds to 470 to indicate that a desired wide margin between the upper pectoral edge and the upper outer breast edge is not achieved. Further, a real-time feedback to adjust one or more of breast position and patient position to obtain the desired wide margin may be provided. The method 400 then returns to 466.

The steps 460 and 466 are based on identifying the pectoral edge from the camera images. The detection of pectoral edge may be determined as discussed above at 446. However, as also indicated above, if a confidence level of detection of pectoral muscle edge definition on the RGB images is less than a threshold confidence, the pectoral muscle edge definition may be evaluated after x-ray image acquisition. Consequently, the evaluation of lower edge of pectoral muscle (that is, where the lower edge of pectoral muscle is at or below the PNL) at 460 and the evaluation of the margin between the upper pectoral edge and outer breast edge at 466 may be performed after x-ray image acquisition on the x-ray images.

Further, it will be appreciated that in some embodiments, the evaluations performed at steps 446, 460, and 466 may be performed once after x-ray image acquisition on the x-ray images, and not prior to x-ray image acquisition.

If the desired wide margin is present, the answer at 466 is YES, and the method 400 proceeds to 472. At 472, the method 400 includes inferring if all posterior and axillary tissues, including axillary tail are included. In one example, inclusion of posterior tissues may be confirmed based on one or more of a patient position, gantry position, and breast size. For example, the method 400 may determine if the user has pulled the breast tissue based on action recognition from an image sequence obtained with the second vision sensor. Further, from one or more images obtained with the second vision sensor, a distance of the nipple from a detector edge may be determined. The distance may be compared to a threshold distance, the threshold distance determined based on a breast size with larger breasts having a greater threshold distance. For example, for a first smaller breast size, a first threshold distance between a nipple of the first breast and the detector edge may be a first shorter distance in order for the posterior tissues to be included; and for a second larger breast size, a second threshold distance between a nipple of the second breast and the detector edge may be a second greater distance for the corresponding posterior breast tissue to be included; and so on. In another example, the convolutional neural network (CNN) may be trained based on X-ray images and corresponding camera (RGB-D) images for posterior tissue inclusion.

Further, the inclusion of axillary tissues may be based on a contour of the compressed breast outline, and axillary tail outline. The axillary tail shall be located above the detector. Axillary tail may be detected by deep learning methods like mask RCNN methods or by image processing (e.g., pattern matching). If one or more of the posterior and axillary tissues are not included, the answer at 472 is NO, and the method 400 proceeds to 474 to evaluate patient position as discussed above at 448. Continuing on to 476, the method 400 includes indicating to the user that one or more of the posterior and axillary tissues are not included. Further, at 476 real time feedback to adjust one or more of patient position and breast position to include posterior and axillary tissues may be provided. The method 400 then returns to 472.

If all posterior and axillary tissues are included, the answer at 472 is YES, and the method 400 proceeds to 478. At 478, the method 400 includes inferring if inframammary fold (IMF) is included. The inclusion of IMF may be similar to the detection of visibility of intermammary cleft, and thus may be determined as discussed at 432, and will not be repeated here for brevity.

Continuing on, the step 480 for providing real time feedback to adjust breast tissue for IMF visibility when IMF is not detected, the step 482 for inferring if one or more skin folds are detected (after confirming IMF at 480), the steps 488 and 490 for providing real time feedback to reduce skin folds if detected, the step 484 for indicating that the breast and the patient position are confirmed for the MLO view when all the breast position and the patient position parameters for the MLO view are satisfied, and the step 486 for acquiring one or more x-ray images for the MLO view are similar to steps 434, 436, 442, 444, 438, and 440 respectively, and will not be repeated for brevity.

Upon confirming that breast position and the patient position parameters are satisfied, and acquiring one or more compressed breast images for the MLO view, the method 400 ends.

While the methods described herein illustrate evaluating breast position and/or patient position with one or more camera images obtained with one or more of the first vision sensor and the second vision sensor before initiating x-ray image acquisition, it will be appreciated that additionally, breast position monitoring may be performed on the acquired view for evaluating if one or more desired criteria for the respective view has been met. That is, after image acquisition, the x-ray images obtained (after breast position evaluation) may also be evaluated for confirming imaging quality and evaluating if the desired criteria for the desired view are met. Further, one or more of annotations and graphical overlays may be displayed on the acquired images indicting whether or not the one or more desired criteria have been met and the desired changes to the current breast position.

Accordingly, in some embodiments, prior to initiating image acquisition and after initial positioning of the breast (compressed between the compression paddle and the detector) a plurality of breast positioning criteria may be evaluated to determine if the breast is positioned for mammography. The plurality of breast positioning criteria may be based on the type of view (MLO or CC view). The plurality of breast positioning criteria may include one or more overview criteria and/or one or more breast features. The one or more overview criteria for CC view may include a central breast position, a left-right symmetry, an axillary tail presence, and an intermammary cleft presence. The one or more breast features for CC view may include pectoral muscle, lateral and medial tissues, axillary tissues, nipple features, and skin folds. Thus, the evaluation criteria for the one or more breast features for the CC view may include presence of pectoral muscle, inclusion of lateral, medial, and axillary tissues (e.g., axillary tail), central position of nipple and nipple in profile, and absence of skin folds in one or more of caudal area, lateral area, and medial area of the compressed breast. For the MLO view, the one or more overview criteria may include the central breast position, the left-right symmetry, and an amount of breast sagging. The one or more breast features for the MLO view may include pectoral muscle based features, posterior tissues, axillary tissues, inframammary fold (IMF), nipple features, and skin folds. Thus, the evaluation criteria for the one or more breast features for the MLO view may include amount of pectoral muscle, position of pectoral edge with respect nipple line, inclusion of posterior, and axillary tissues (e.g., axillary tail), central position of nipple and nipple in profile, and absence of skin folds in one or more of IMF area, pectoral area, and axilla area of the compressed breast.

In one example, the plurality of breast positioning criteria may be evaluated in a desired order. Based on the evaluation of the plurality of breast positioning criteria, real-time feedback based on the evaluation of each criteria may be provided to assist the user in positioning the breast. In this way, proper positioning of the breast for mammography for each view may be achieved.

In another example, in addition to evaluating the plurality of breast positioning criteria, at each step patient position may be evaluated. Based on the evaluation of breast features and patient evaluation, real-time feedback based on the evaluation of each feature may be provided to assist the user in positioning the breast.

In this way, proper positioning of the breast for mammography for each view may be achieved. Further, by performing step-by step evaluation of breast structures and patient position prior to x-ray image acquisition, image processing speed is increased, and improves feedback speed, which in turn results in overall improvement of breast positioning efficiency.

Further, after adjusting one or more of the patient position and the breast position based on the evaluation of one or more of the patient position and the breast position, the x-ray system may proceed to acquire one or more x-ray images. Additionally, the one or more acquired x-ray images may be evaluated for one or more of the plurality of the breast positioning criteria. Thus, a first evaluation may be performed with the camera images (e.g., RGB-depth images) acquired by one or more of the first vision sensor and the second vision sensor, and a second evaluation may be performed with one or more x-ray images acquired with the x-ray system. During the second evaluation with the x-ray images, one or more of the plurality of breast position criteria may be evaluated simultaneously. For example, during the second evaluation, the acquired x-ray images may be evaluated for one or more overview criteria and/or one or more breast features (corresponding to the view) simultaneously. Further, feedback to the user may be provided via one or more of annotations and overlays on the acquired x-ray images.

In some other embodiments, during the first evaluation with the camera images, the one or more overview criteria for CC view may include a central breast position, a left-right symmetry, and an intermammary cleft presence. The one or more breast features for CC view may include nipple features, and skin folds. Thus, the evaluation criteria during the first evaluation for the one or more breast features for the CC view may include the central position of nipple and nipple in profile, and absence of skin folds in one or more of caudal area, lateral area, and medial area of the compressed breast (first set of features). During the second evaluation with the x-ray images the features that were not evaluated during the first evaluation such as presence of axillary tail, presence of pectoral muscle, inclusion of lateral, medial, and axillary tissues (second set of features) may be evaluated. Similarly, MLO view may be evaluated with a first set of features evaluated during the first evaluation and a second set of features, different from the first set of features, evaluated during the second evaluation. In some examples, the first set and the second set of features may be evaluated during the second evaluation.

In this way, proper positioning of the breast for mammography for each view may be achieved. Further, by performing step-by step evaluation of breast structures and patient position prior to x-ray image acquisition, image processing speed is increased, and improves feedback speed, which in turn results in overall improvement of breast positioning efficiency.

In some embodiments, one or more of the breast positioning error and patient positioning error may be detected based on a movement recognition of one or more of the patient and a user (that is, the technologist performing the mammography). For example, the breast has to be pulled in a particular manner to position the breast. Therefore, the gesture of the technologist may be analyzed to check whether the user has pulled the breast.

Figure 5:
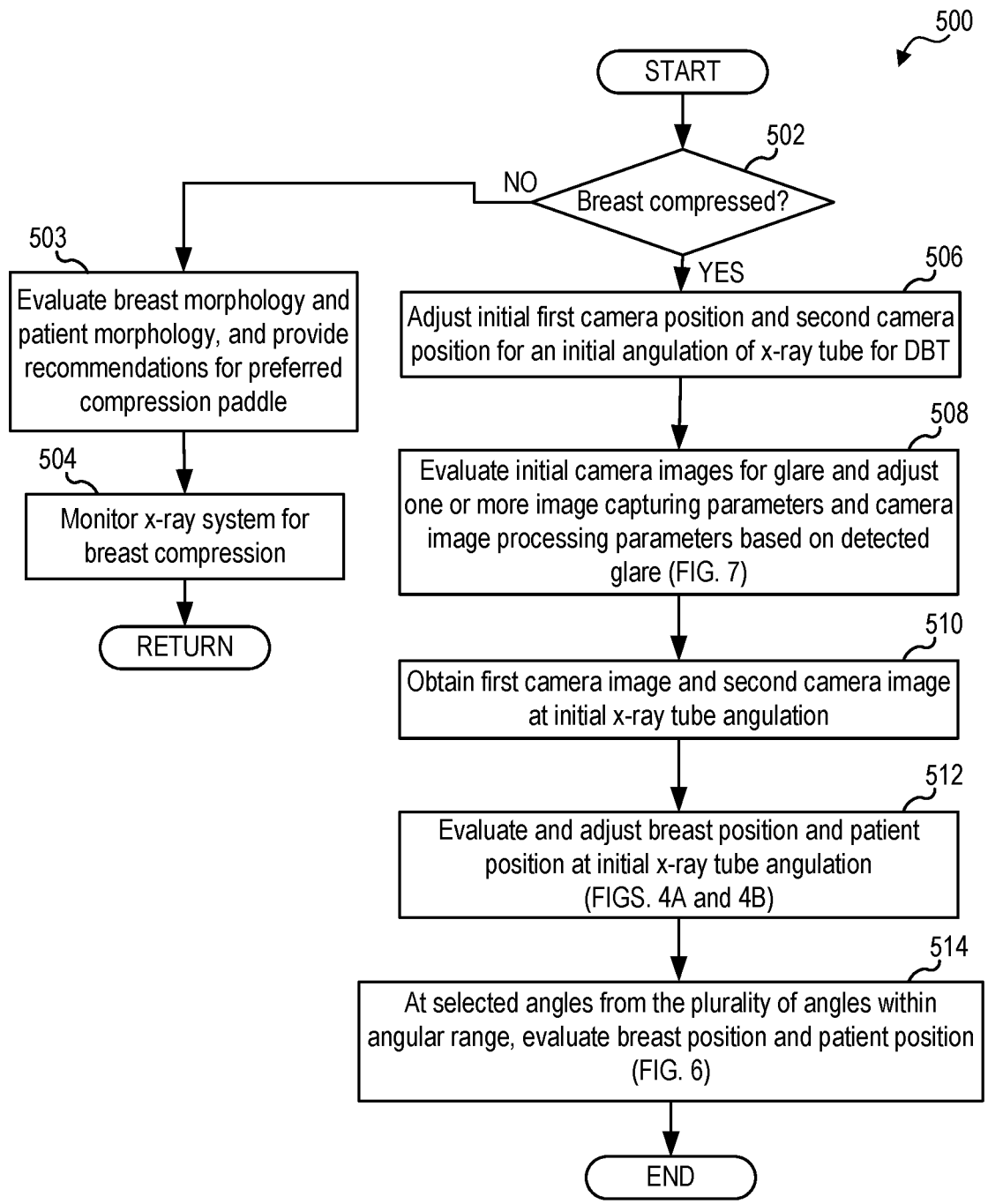
FIG. 5 is a high-level flow chart illustrating a method for evaluating breast position and breast morphology during Digital Breast Tomosynthesis (DBT) and providing real-time feedback for adjusting breast position and patient position for improving DBT image quality, according to an embodiment of the disclosure.

Turning to FIG. 5, a high-level flow chart illustrating a method 500 for evaluating breast position and breast morphology during Digital Breast Tomosynthesis (DBT) is shown. The method 500 may be performed prior to initiating x-ray image acquisition in order to determine if the desired breast position for DBT is achieved. The breast position evaluation may be performed based on input from a second vision sensor, such as the camera 154 at FIG. 1B, and the patient position evaluation may be performed based on input from one or more of the second vision sensor and a first vision sensor, such as camera at FIG. 1A. The method 500 may be implemented by an image processing system, such as controller 44 at FIG. 1A, an edge device connected to the image processing system, a cloud in communication with the image processing system, or any appropriate combination thereof. Method 500 is described with regard to the systems and components of FIGS. 1A, 1B, and 1C, although it should be appreciated that method 500 may be implemented with other systems and components without departing from the scope of the present disclosure.

The method 500 begins at 502. Steps 502, 503, 504, 506, and 508 are similar to steps 402, 404, 405, 406, and 408 at FIG. 4A, and hence, will not be repeated for brevity. Briefly, the above-steps of method 500 includes monitoring the x-ray system for breast compression, and after compression, the first vision sensor and the second vision sensor are adjusted at an initial angulation for DBT acquisition. In one example, the initial angulation position, may be the first vision sensor position and the second vision sensor position for CC view. In another example, the initial angulation position may be the first vision sensor position and the second vision sensor position for MLO view. It will be appreciated that the initial angulation for DBT may be any selected angle of the x-ray source, and the first and the second vision sensor may be adjusted accordingly. Upon adjusting the first vision sensor and the second vision sensor, one or more initial camera images from the first and the second vision sensor may be obtained, evaluated for glare, and one or more image capturing parameters and camera image processing parameters may be adjusted based on detected glare.

Continuing on to 510, the method 500 includes obtaining a first camera from the first vision sensor and a second camera image from the second vision sensor with the x-ray source is at the initial angulation for DBT after adjusting for glare.

Next, at 512, the method 500 includes evaluating breast position and patient position at the initial angulation, and adjusting the breast position and patient position based on real-time feedback from the evaluation, as discussed at FIGS. 4A and 4B. Briefly, the method 500 may evaluate breast position based on identified breast structures from the second camera image obtained with the second vision sensor and the patient position from the first camera image obtained with the first vision sensor. The breast structures and the patient positions evaluated are based on the initial angulation of the x-ray tube. For example, if the initial angulation is zero degree angulation of the x-ray source, the breast position and the patient position evaluation may include step-wise evaluation of pectoralis muscle inclusion, lateral and medial tissues inclusion, nipple profile confirmation, IMF inclusion, and absence of one or more skin and fat folds. At each evaluation step, real-time feedback may be provided to adjust one or more of breast position and patient position to ensure the breast and the patient are at the desired position. Similarly, if the initial angulation is MLO view angulation (e.g., 45 degree x-ray source angulation), the breast position and the patient position evaluation may include step-wise evaluation of pectoral muscle edge shape and position, nipple profile confirmation, margin between upper pectoral muscle edge and upper outer breast edge, posterior and axillary tissue inclusion, IMF inclusion, and absence of one or more skin and fat folds. As discussed above, at each step real-time feedback to adjust one or more of breast position and patient position may be provided to the user.

Upon adjusting the breast position and the patient position at the initial x-ray tube angulation, the method 500 proceeds to 514. At 514, the method 500 includes at selected angles from a plurality of angles within the angular range for DBT acquisition, evaluating breast position and patient position, and providing real-time feedback to the user based on the breast position and the patient position evaluation. Details of evaluating breast position and patient position for DBT is discussed at FIG. 6.

Figure 6:
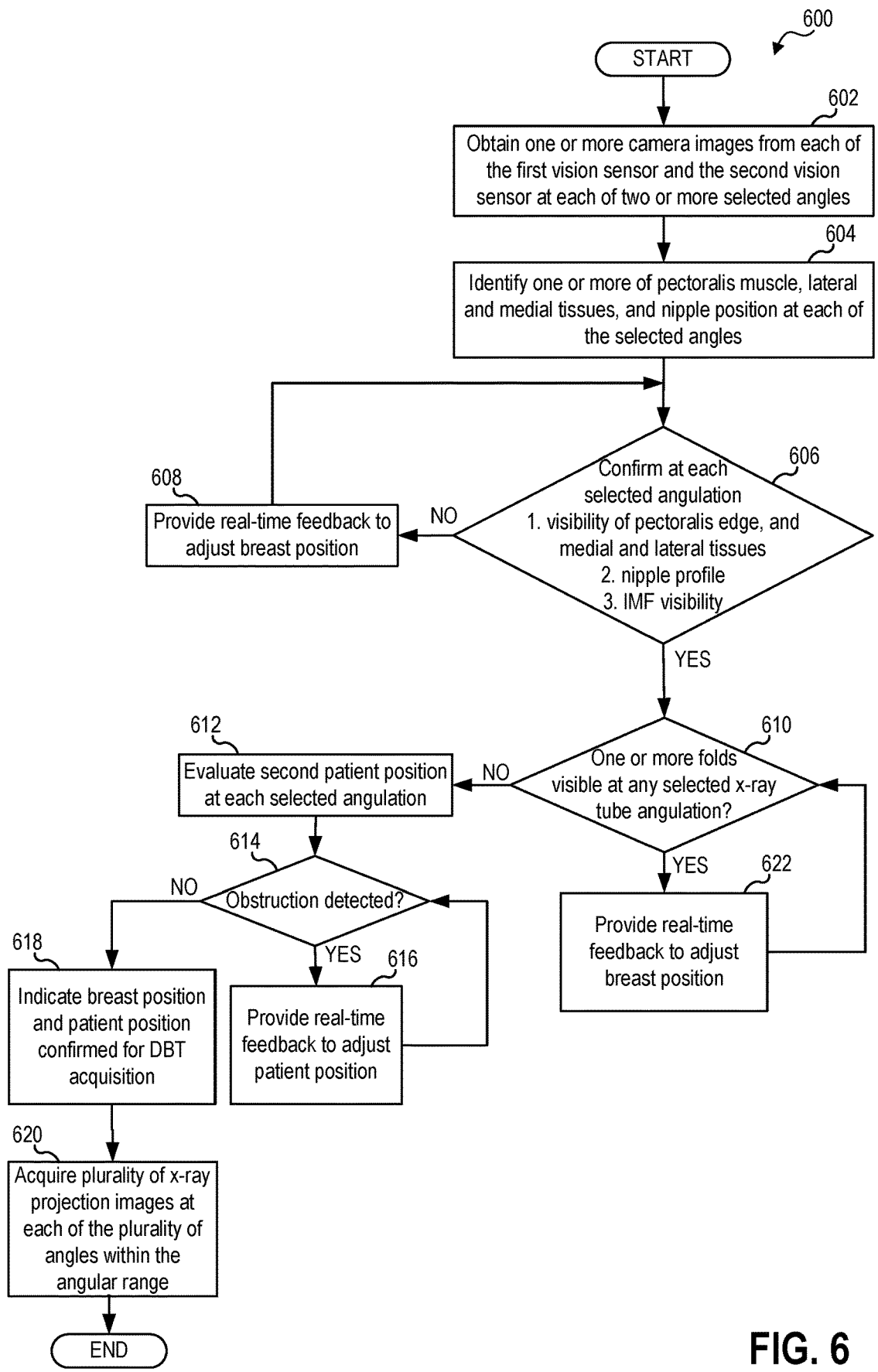
FIG. 6 is a high-level flow chart illustrating a method for evaluating breast position and patient position during DBT imaging at select angles within an angular range of the x-ray system, and providing real-time feedback for adjusting breast position and patient position for improving DBT image quality, according to an embodiment of the disclosure.

Turning to FIG. 6, a high-level flow chart illustrating a method 600 for evaluating breast position and patient position during DBT imaging at two or more select angles within an angular range of the x-ray system, and providing real-time feedback for adjusting breast position for DBT acquisition, is shown. Further, the method 600 includes evaluating patient position to detect obstructions (e.g., patient body part that is not imaged) when the gantry moves at plurality of angles for DBT acquisition. The method 600 may be performed prior to initiating x-ray image acquisition in order to determine if the desired breast position and patient body position for DBT is achieved. The breast position evaluation may be performed based on input from a second vision sensor, such as the camera 154 at FIG. 1B, and the patient position evaluation may be performed based on input from one or more of the second vision sensor and a first vision sensor, such as camera at FIG. 1A. The method 600 may be implemented by an image processing system, such as controller 44 at FIG. 1A, an edge device connected to the image processing system, a cloud in communication with the image processing system, or any appropriate combination thereof. Method 600 is described with regard to the systems and components of FIGS. 1A, 1B, and 1C, although it should be appreciated that method 600 may be implemented with other systems and components without departing from the scope of the present disclosure. The method 600 will be described for DBT acquisitions wherein the x-ray source is rotated around the compressed breast within an angular rotation range (+θ to −θ) about a medial position at which a vertical axis of the x-ray system, such as vertical axis 60 at FIG. 1A, is perpendicular to the detector. Other DBT acquisitions wherein the x-ray source is rotated about an axis angled with respect to the vertical axis (e.g. at 30 degrees, 45 degrees, 60 degrees, etc. from the medial position) are also within the scope of the disclosure.

The method 600 begins at 602. At 602, the method 600 includes obtaining one or more camera images from each of the first vision sensor and the second vision sensor at each of two or more selected angles. The selected angles include various angulations of the x-ray source at which projection images for DBT are obtained, and as such, the breast position and patient position are evaluated at the selected angles. Accordingly, in one example, each of the plurality of angles at which the DBT acquisition is performed may be selected for evaluation of breast position and patient position. In another example, breast position and patient position evaluation may be performed for two or more number of angulations but less than the total number of angles at which the projection images are obtained for DBT. For example, the end angulations in either direction (+θ or −θ) may be selected along with the medial position. In some examples, in addition to the end angulations and the medial position, one or more angulations in between may be selected for evaluation of breast position and patient position for subsequent DBT acquisition.

Next, at 604, the method 600 includes identifying from one or more camera images obtained with the second sensor, at each of the selected angulations, a visible edge of pectoralis muscle, lateral and medial tissues, and nipple position. For example, the one or more camera images obtained with the second vision sensor may be input into an artificial intelligence based neural network model for identifying anatomical landmarks of the compressed breast, including the visible edge of the pectoralis muscle, lateral and medial tissues, and nipple position. In one example, an output of the AI based neural network model may include one or more segmented camera images with annotations for the above-mentioned anatomical landmarks of the compressed breast.

Continuing on to 606, the method 600 includes confirming at each selected angulation, visibility of pectoralis edge, lateral and medial tissue inclusion, confirmation of nipple profile and central positioning of the nipple (that is not pointing medially or laterally), and IMF visibility. If visibility and positioning of all of the above anatomical structures are confirmed at each of the two or more selected angles, the answer at 606 is YES, and the method proceeds to 610. If any of the above anatomical landmarks of the breast are not confirmed, the answer at 606 is NO, and the method 600 proceeds to 608. At 608, the method 600 includes providing real-time feedback to adjust breast position such that the pectoralis edge is visible, lateral and medial tissues are included, nipple profile is visible and the nipple is centrally positioned, and the IMF is visible. Additionally, in some examples, patient body position from one or more camera images obtained with the first vision sensor may be evaluated at each of the two or more selected angulations. In particular, evaluating patient body position includes determining if a patient shoulder distance from the x-ray system is within a threshold distance, a patient head position including a level of tilt is less than a threshold tilt and direction of head turn is towards the contralateral side, a patient feet position is pointing towards the x-ray system, a body rotation is towards a medial position, and a patient spine position is angled from the hip. If any of the above patient body parameters are not met, the real-time feedback may include adjusting the patient position based on patient body position evaluation in addition to the breast position based on the breast anatomical structures.

In one example, each of the breast anatomical structures including the pectoralis muscle, lateral and medial tissues, nipple, and IMF may be evaluated step by step along with patient body position. For example, the pectoralis muscle is first evaluated along with patient body position, and upon providing feedback to adjust one or more of breast position and patient body position for visibility of pectoralis muscles, and subsequently confirming inclusion of the pectoralis muscle, the method proceeds to evaluate the lateral and medial tissues along with the patient body position. Upon providing feedback to adjust one or more of breast position and patient body position to include lateral and medial tissues, and confirming inclusion of the lateral and medial tissues, the method proceeds to evaluate nipple profile and position. Upon providing feedback to adjust nipple profile and position, and confirming desired positioning of the nipple and confirmation of the nipple profile, the method proceeds to evaluate if IMF is visible. Upon providing feedback to adjust one or more of breast position and patient position to include IMF, and confirming inclusion of the IMF, the method may proceed to the next step 610.

Continuing on to 610, the method 600 includes determining if one or more folds, such as skin folds, fat folds, etc., are visible at each of the selected x-ray tube angulations. If YES, at 622, the method 600 includes providing real-time feedback to adjust breast position to reduce the occurrence of folds. The method 600 then returns to monitor for folds. If one or more folds are not visible, the method 600 proceeds to 612.

At 612, the method 600 includes evaluating second patient position at each selected angulation. The evaluation of second patient position may be based on one or more camera images obtained from the second vision sensor after adjusting breast position and patient body position for inclusion of anatomical landmarks and reduction of folds. Evaluating second patient position includes evaluating a patient ipsilateral and contralateral shoulder position, a patient head position, and a contralateral breast position. In particular, it may be determined if any of the patient ipsilateral shoulder, contralateral shoulder, patient head, and contralateral breast are in the field of view of the x-ray source at each of the two or more selected angulations such that a portion of field of view is obstructed by the patient's body part. The second vision sensor captures the field of view of the x-ray source, and as such the second patient position evaluation may be performed using one or more camera images obtained with the second vision sensor. During the second patient position evaluation, the one or more camera images obtained with the second vision sensor at each of the selected angles may be input into an artificial intelligence based algorithm trained to identify obstructing portions of the patient's body in the one or more camera images. For example, if a portion of the contralateral breast is visible at one or more selected angles, the algorithm may identify the obstructing portion and the angulation at which the obstruction is identified, and indicate the identified obstruction on the one or more camera images.

Continuing on to 614, the method 600 includes confirming if obstruction is detected based on evaluation of the second patient position as discussed at 612. If the answer at 614 is YES, the method 600 proceeds to 616 to provide real-time feedback to adjust patient position to move the obstructing body part away from the field of view, without changing the compressed breast position. The method 600 then returns to 614 to verify if the obstruction is cleared after adjustment of patient position.

If the obstruction is not detected, the answer at 614 is NO, and the method proceeds to 618 to indicate, via the user interface, that the breast position and patient position are confirmed for DBT acquisition.

Continuing on to 620, the method 600 includes performing DBT by acquiring a plurality of x-ray projection images at each of the plurality of angles.

In this way, prior to DBT acquisitions, the breast position and the patient position may be evaluated based on camera images from the first vision sensor (for patient body position evaluation) and the second vision sensor (for breast position evaluation and obstruction identification) at two or more selected angulations within the angular range of the x-ray source rotation for DBT. By evaluating breast position and patient position at more than one angulation of the x-ray source, breast positioning and patient positioning errors that may not be easily detected in just one angulation may be identified, and real time feedback to adjust one or more of breast and patient position may be provided. As a result, quality and consistency of DBT may be improved. Further, by identifying and correcting positioning errors prior to acquisitions, the need for recall is reduced, which in turn reduces radiation exposure to the patient, and improves patient comfort and confidence in diagnosis.

While the above method 600 describes performing a DBT sweet without x-ray imaging, and evaluating one or more of breast position and patient position at two or more x-ray source angulations prior to initiating the DBT acquisition with x-ray, in some embodiments, the one or more of breast and patient positions may be evaluated at a plurality of DBT angulations without moving the x-ray tube, and real-time feedback may be provided based on the evaluation (prior to DBT acquisition with x-ray). In one example, position of the second vision sensor may be adjusted without moving the gantry to evaluate one or more of the breast and patient positions at the plurality of DBT angulations. In another example, the evaluation of one or more of the breast position and patient position for plurality of angulations for DBT may be performed at a single camera position and a single gantry position.

In one embodiment, a set of breast features may be evaluated to determine if the breast is positioned for mammography. The set of breast features may be based on the type of view (MLO or CC view). Further, the set of breast features may include tissue features, nipple features, mammary fold, and skin folds. In one example, the set of breast features may be evaluated in a desired order, and at each step patient position may be evaluated. Based on the evaluation of breast features and patient evaluation, real-time feedback based on the evaluation of each feature may be provided to assist the user in positioning the breast. For example, first the pectoralis muscle may be identified and confirmed to be present in the field of view of the camera. Upon confirming the presence of pectoralis muscle, the controller may determine is all lateral and medial tissues are included. Next, nipple position may be evaluated, followed by identification of the inframammary fold. Finally, upon ensuring proper positioning of the breast with respect to the tissues, nipple position, and IMF, the controller may evaluate of one or more skin fold are visible. At each step, if the corresponding feature is not detected or properly positioned, the controller may provide real-time feedback to adjust one or more of the breast and the patient. In this way, proper positioning of the breast for mammography for each view may be achieved. Further, by performing step-by step evaluation of breast structures and patient position, image processing speed is increased, and improves feedback speed, which in turn results in overall improvement of breast positioning efficiency.

Next, FIG. 7 shows a high-level flow chart illustrating a method 700 for reducing glare in a camera image obtained with a vision sensor coupled to a mammography system, such as the mammography system 100 at FIG. 1A. The vision sensor may be the first vision sensor 101 at FIG. 1A, the second vision sensor 154 at FIG. 1B, or any camera coupled to the mammography system. The first and the second vision sensor are utilized to obtain patient image and compressed breast image, which are then utilized to evaluate one or more of a patient position and breast position based on patient morphology and breast anatomical structural landmarks. Thus, prior to evaluating breast and patient position from the camera images, the camera images may be analyzed for glare and processed to reduce glare, if detected, in order to improve downstream analysis of the camera images. The method 700 may be implemented by an image processing system, such as controller 44 at FIG. 1A, an edge device connected to the image processing system, a cloud in communication with the image processing system, or any appropriate combination thereof. The method 700 described herein are discussed with regard to the systems and components of FIG. 1A-1D, although it should be appreciated that method may be implemented with other systems and components without departing from the scope of the present disclosure. The method 700 will be described with respect to a camera image, and it will be appreciated that the method 700 for detecting and reducing glare may be applied to any camera image obtained with any vision sensor.

Method 700 begins at 702. At 702, the method 700 includes obtaining a camera image, and identifying a region of interest for the camera image. The region of interest may include an area on the camera image that is subject to further processing for position evaluation. For example, if a camera image from the first vision sensor (used for patient position evaluation) is obtained, the region of interest may include a portion of camera image including the patient and the x-ray system. If a camera image from the second vision sensor (used for identifying breast anatomical landmarks, and thus, breast position evaluation) is obtained, the region of interest may include a portion of the camera image including the compressed breast.

Next, at 704, the method 700 includes determining if glare is detected within the region of interest. Glare may be detected based on photometric features including one or more light intensity, color saturation, and luminance contrast. For example, regions of the camera image having light intensity greater than a threshold intensity, color saturation less than a threshold saturation level, and luminance contrast less than a threshold contrast level may indicate glare regions. If glare is not detected within the region of interest or detected outside the region of interest, the method 700 proceeds to 708 to indicate that glare adjustments are not required, and the method 700 ends. If glare is detected within the region of interest, the method 700 proceeds to 706.

At 706, the method 700 includes indicating the regions within the region of interest that include glare. Next, at 708, the method 700 includes providing feedback to the user to reduce glare. The feedback may include, at 712, instructions to adjust camera position; at 714, instructions to adjust room lighting to reposition the glare source (which is typically a light source) such that the glare region is not within the region of interest; at 716, instructions to include or adjust a polarizing filter on the camera lens. Further, in some examples, glare may be reduced by adjusting one or more camera image capturing parameters (e.g., by commanding a camera controller to adjust one or more camera image capturing parameters) including a camera position, a room lighting, and a polarization filter, and camera image processing parameters based on an amount and a location of each of the one or more glare areas to reduce glare.

Upon providing feedback, the method 700 proceeds to 718. At 718, the method 700 includes confirming if glare is removed within the region of interest. If answer at 718 is YES, the method 700 proceeds to 708 to indicate that the glare adjustments are complete, and the method 700 end. However, if the glare is not moved away from the region of interest or reduced below a threshold amount, the method 718 proceeds to 720.

At 720, the method 700 includes determining a number of images and camera settings (e.g., reduced exposure) for the number of images to generate a composite image with reduced glare in the region of interest.

Continuing on to 722, the method 700 includes utilizing the composite image for subsequent breast position and/or patient positioning evaluation.

A technical effect of the present disclosure includes improved and real-time breast positioning evaluation, guidance, and feedback prior to image acquisition, thereby resulting in higher quality x-ray mammography images without repeated and/or increased exposure to the patient. Another technical effect is improved diagnostic capability resulting from improved breast positioning and thus, reduced need for recall. Yet another technical effect is automated guidance for novice user so as to obtain higher quality mammography images.

In one embodiment, a method for an x-ray mammography system comprises evaluating, via vision sensing using one or more cameras coupled to the x-ray mammography system, one or more of a patient position of a patient, a partial view of the patient, and a breast anatomy of the patient; detecting one or more of a patient positioning error and a breast positioning error based on the evaluation; and providing real-time feedback to a user based on the detection via a user interface of the mammography system. In a first example of the method, the method may additionally or alternatively include wherein the breast anatomy is evaluated with a camera having a field of view including an imaging volume between a compression paddle and a detector of the x-ray mammography system. A second example of the method optionally includes the first example, and further includes wherein the patient position is evaluated based on input from a first camera having a first field of view of the x-ray mammography system and the patient, and the breast anatomy is evaluated based on input from a second camera having a second field of view including an imaging volume between a compression paddle and a detector of the x-ray mammography system. A third example of the method optionally includes one or more of the first and the second examples, and further includes wherein evaluating patient position includes evaluating a patient shoulder distance from the x-ray system, a patient head position, a patient feet position, a patient posture, a patient body rotation, and a patient spine position. A fourth example of the method optionally includes one or more of the first through the third examples, and further includes wherein the one or more of patient positioning error and the breast positioning error are detected prior to image acquisition by the x-ray mammography system. A fifth example of the method optionally includes one or more of the first through the fourth examples, and further includes wherein the patient positioning error is based on one or more of a patient skeletal model and a relative position of the patient with respect to the x-ray mammography system. A sixth example of the method optionally includes one or more of the first through the fifth examples, and further includes wherein the breast positioning error is based on a desired acquisition view, and one or more breast anatomical features of a breast in the imaging volume. A seventh example of the method optionally includes one or more of the first through the sixth examples, and further includes wherein one or more of the breast positioning error and patient positioning error is detected based on a movement recognition of one or more of the patient and a user. An eighth example of the method optionally includes one or more of the first through the seventh examples, and further includes when the desired acquisition view is a craniocaudal view, evaluating the breast anatomy includes detecting one or more of pectoralis muscle inclusion, breast centering, nipple position, intermammary cleft inclusion, and one or more skin and fat fold absence; and providing real time feedback based on each detection; and when the desired acquisition view is a mediolateral oblique view, evaluating the breast anatomy includes detecting one or more of pectoral muscle position, nipple position, axillary tissue inclusion, inframammary fold inclusion, and one or more skin and fat fold absence; and providing real time feedback based on each detection. A ninth example of the method optionally includes one or more of the first through the eighth examples, and further includes during one or more of a quality check mode and a cleaning mode of operation of the x-ray mammography system, evaluating, via the vision sensing using the one or more cameras, a user morphology and a user position; and adjusting one or more components of the x-ray mammography system based on the user morphology and the user position; and wherein the one or more components include a position of a compression paddle holder on gantry rails of the x-ray mammography system, a x-ray system height and a control station height of a workstation. A tenth example of the method optionally includes one or more of the first through the ninth examples, and further includes before compressing a patient breast, evaluating, via the vision sensing using the one or more cameras, a patient morphology and a breast morphology of the patient; and identifying a preferred compression paddle based on the patient morphology and the breast morphology; and indicating the preferred compression paddle on the user interface. An eleventh example of the method optionally includes one or more of the first through the tenth examples, and further includes before compressing a patient breast, evaluating, via the vision sensing using the one or more cameras, a patient morphology and a breast morphology of the patient; and adjusting a support table position on the x-ray mammography system based on the patient morphology and the breast morphology.

In another embodiment, a method for an x-ray mammography system comprises determining a current mode of operation, evaluating, via a vision system including one or more vision sensors, a breast position of a breast in an imaging volume of the x-ray mammography system and a patient position based on the current mode; detecting one or more of a patient positioning error, and a breast positioning error based on the evaluation; and providing real-time feedback including indications for one or more of desired breast position and desired patient position based on the detection via a user interface of the mammography system; wherein the patient positioning error is detected based on a patient anatomy and a patient position with respect to the x-ray mammography system; and wherein the breast positioning error is detected based on one or more anatomical structures of the breast. In a first example of the method, the method may additionally or alternatively include when the current mode is a digital breast tomosynthesis mode, evaluating one or more of the breast positioning error and the patient positioning error at one or more x-ray source angulations within an angular range of the x-ray mammography system prior to initiating tomosynthesis acquisition. A second example of the method optionally includes the first example, and further includes initiating x-ray image acquisition for the current mode; detecting a movement of the patient during the x-ray image acquisition; and indicating an error due to a patient position change in response to the detection; wherein the current mode is one of a digital breast tomosynthesis mode and an image guided biopsy mode. A third example of the method optionally includes one or more of the first and the second examples, and further includes wherein the patient position is evaluated based on a first camera image from a first vision sensor of the vision system having a first field of view of the x-ray mammography system and the patient, and the breast position is evaluated based on a second camera image from a second vision sensor of the vision system having a second field of view including an imaging volume between a compression paddle and a detector of the x-ray mammography system. A fourth example of the method optionally includes one or more of the first through the third examples, and further includes wherein the first vision sensor and the second vision sensor are each RGB-depth type vision sensors, and wherein indications for one or more of desired breast position and desired patient position are provided on the first camera image and the second camera image respectively; and further comprising, prior to evaluating the patient position and the breast position, evaluating the first field of view of the first sensor and the second field of view of the second vision sensor for one or more glare areas. A fifth example of the method optionally includes one or more of the first through the fourth examples, and further includes acquiring x-ray images of the breast; detecting one or more second breast positioning errors based on the acquired x-ray images; and providing second feedback including second indications on the acquired x-ray image, the second indications including the second breast positioning errors and one or more desired breast structures to be imaged; wherein the second feedback is provided via the user interface of the mammography system.

The systems and methods described above also provide for a medical imaging system, comprising: a gantry including a radiation source for emitting radiation rays, a detector for receiving the radiation rays, and a collimator for adjusting a field of view; a vision sensor system including at least a first vision sensor and a second vision sensor; and a workstation including a first user interface including a first display portion, the workstation communicatively coupled to the gantry, the gantry coupled to a second user interface including a second display portion; and wherein the workstation includes a processor, the processor configured with instructions in non-transitory memory that when executed cause the processor to: acquire, with the first vision sensor, a first camera image of a patient and the medical imaging system; acquire, with the second vision sensor, a second camera image of a breast in an imaging volume of the medical imaging system; determine, with the first camera image and the second camera image, a patient position with respect to the medical imaging system, and a breast position with respect to a whole body position of a patient and the medical imaging system and based on a patient breast anatomy; responsive to the patient position in agreement with a first model and the breast position in agreement with a second model initiating image acquisition; otherwise, providing real-time feedback via the first and the second user interface of the medical imaging system and inhibiting image acquisition with the radiation source until the patient position is in agreement with the first model and the breast position is in agreement with the second model; and providing an option, via one or more of the first user interface and the second interface, for a user to initiate image acquisition when one or more of the patient position is not in agreement with the first model and the breast position is not in agreement with the second model; wherein the first model and the second model are based on an artificial intelligence algorithm using the first camera image and the second camera image as inputs. In a first example of the system, the system may additionally or alternatively include wherein the first vision sensor has a first field of view of the medical imaging system and the patient, and the second vision sensor has a second field of view of an imaging volume of the medical imaging system; and wherein the first model is based on one or more of a patient skeletal model and a relative position of the patient with respect to the medical imaging system; and wherein the second model is based on a desired acquisition view, and one or more breast anatomical features of a breast in the imaging volume.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an x-ray mammography system comprising:
   providing the x-ray mammography system with a user interface and one or more cameras coupled to the x-ray mammography system;
   evaluating, via vision sensing using one or more cameras coupled to the x-ray mammography system, one or more of a patient position of a patient, a partial view of the patient, and a breast anatomy of the patient;
   detecting one or more of a patient positioning error and a breast positioning error based on the evaluation; and
   providing, via the user interface of the mammography system, real-time feedback to a user based on the detection and further based at least in part on an artificial intelligence based image processing model that uses images from the one or more cameras.

2. The method of claim 1, wherein the breast anatomy is evaluated with a camera having a field of view including an imaging volume between a compression paddle and a detector of the x-ray mammography system.

3. The method of claim 1, wherein the patient position is evaluated based on input from a first camera having a first field of view of the x-ray mammography system and the patient, and the breast anatomy is evaluated based on input from a second camera having a second field of view including an imaging volume between a compression paddle and a detector of the x-ray mammography system.

4. The method of claim 1, wherein evaluating patient position includes evaluating a patient shoulder distance from the x-ray mammography system, a patient head position, a patient feet position, a patient posture, a patient body rotation, and a patient spine position.

5. The method of claim 1, wherein the one or more of patient positioning error and the breast positioning error are detected prior to image acquisition by the x-ray mammography system.

6. The method of claim 1, wherein the patient positioning error is based on one or more of a patient skeletal model and a relative position of the patient with respect to the x-ray mammography system.

7. The method of claim 1, wherein the breast positioning error is based on a desired acquisition view, and one or more breast anatomical features of a breast in the imaging volume.

8. The method of claim 1, wherein one or more of the breast positioning error and patient positioning error is detected based on a movement recognition of one or more of the patient and a user.

9. The method of claim 1, further comprising:
   during one or more of a quality check mode and a cleaning mode of operation of the x-ray mammography system,
   evaluating, via the vision sensing using the one or more cameras, a user morphology and a user position; and
   adjusting one or more components of the x-ray mammography system based on the user morphology and the user position;
   wherein the one or more components include a position of a compression paddle holder on gantry rails of the x-ray mammography system, an x-ray system height and a control station height of a workstation.

10. The method of claim 1, further comprising:
    before compressing a patient breast,
    evaluating, via the vision sensing using the one or more cameras, a patient morphology and a breast morphology of the patient;
    identifying a preferred compression paddle based on the patient morphology and the breast morphology; and
    indicating the preferred compression paddle on the user interface.

11. The method of claim 1, further comprising:
    before compressing a patient breast,
    evaluating, via the vision sensing using the one or more cameras, a patient morphology and a breast morphology of the patient; and
    adjusting a support table position on the x-ray mammography system based on the patient morphology and the breast morphology.

12. The method of claim 7, when the desired acquisition view is a craniocaudal view, evaluating the breast anatomy includes detecting one or more of pectoralis muscle inclusion, breast centering, nipple position, intermammary cleft inclusion, and one or more skin and fat fold absence; and providing real time feedback based on each detection; and when the desired acquisition view is a mediolateral oblique view, evaluating the breast anatomy includes detecting one or more of pectoral muscle position, nipple position, axillary tissue inclusion, inframammary fold inclusion, and one or more skin and fat fold absence; and providing real time feedback based on each detection.

13. A method for an x-ray mammography system comprising:
    providing a vision system including one or more vision sensors and the x-ray mammography system including a user interface;
    determining a current mode of operation;
    evaluating, via the vision system including one or more vision sensors, a breast position of a breast in an imaging volume of the x-ray mammography system and a patient position based on the current mode;

detecting one or more of a patient positioning error, and a breast positioning error based on the evaluation; and providing real-time feedback including indications for one or more of desired breast position and desired patient position based on the detection via the user interface of the mammography system;

wherein the patient positioning error is detected based on a patient anatomy and a patient position with respect to the x-ray mammography system;

wherein the breast positioning error is detected based on one or more anatomical structures of the breast; and wherein when the current mode is a digital breast tomosynthesis mode, evaluating one or more of the breast positioning error and the patient positioning error at one or more x-ray source angulations within an angular range of the x-ray mammography system prior to initiating tomosynthesis acquisition.

14. The method of claim 13, further comprising:
initiating x-ray image acquisition for the current mode;
detecting a movement of the patient during the x-ray image acquisition; and
indicating an error due to a patient position change in response to the detection;
wherein the current mode is one of a digital breast tomosynthesis mode and an image guided biopsy mode.

15. The method of claim 13, wherein the patient position is evaluated based on a first camera image from a first vision sensor of the vision system having a first field of view of the x-ray mammography system and the patient, and the breast position is evaluated based on a second camera image from a second vision sensor of the vision system having a second field of view including an imaging volume between a compression paddle and a detector of the x-ray mammography system.

16. The method of claim 13, further comprising:
acquiring x-ray images of the breast;
detecting one or more second breast positioning errors based on the acquired x-ray images; and
providing second feedback including second indications on the acquired x-ray image, the second indications including the second breast positioning errors and one or more desired breast structures to be imaged;
wherein the second feedback is provided via the user interface of the mammography system.

17. The method of claim 15, wherein the first vision sensor and the second vision sensor are each RGB-depth type vision sensors, and wherein indications for one or more of desired breast position and desired patient position are provided on the first camera image and the second camera image respectively; and further comprising, prior to evaluating the patient position and the breast position, evaluating the first field of view of the first sensor and the second field of view of the second vision sensor for one or more glare areas.

18. A medical imaging system, comprising:
a gantry including a radiation source for emitting radiation rays, a detector for receiving the radiation rays, and a collimator for adjusting a field of view;
a vision sensor system including at least a first vision sensor and a second vision sensor; and
a workstation including a first user interface including a first display portion, the workstation communicatively coupled to the gantry, the gantry coupled to a second user interface including a second display portion;
wherein the workstation includes a processor, the processor configured with instructions in non-transitory memory that when executed cause the processor to:
acquire, with the first vision sensor, a first camera image of a patient and the medical imaging system;
acquire, with the second vision sensor, a second camera image of a breast in an imaging volume of the medical imaging system;
determine, with the first camera image and the second camera image, a patient position with respect to the medical imaging system, and a breast position with respect to a whole body position of a patient and the medical imaging system and based on a patient breast anatomy;
responsive to the patient position in agreement with a first model and the breast position in agreement with a second model, initiate image acquisition; otherwise, provide real-time feedback via the first and the second user interface of the medical imaging system and inhibiting image acquisition with the radiation source until the patient position is in agreement with the first model and the breast position is in agreement with the second model; and
provide an option, via one or more of the first user interface and the second interface, for a user to initiate image acquisition when one or more of the patient position is not in agreement with the first model and the breast position is not in agreement with the second model;
wherein the first model and the second model are based on an artificial intelligence algorithm using the first camera image and the second camera image as inputs.

19. The system of claim 18, wherein the first vision sensor has a first field of view of the medical imaging system and the patient, and the second vision sensor has a second field of view of an imaging volume of the medical imaging system; and wherein the first model is based on one or more of a patient skeletal model and a relative position of the patient with respect to the medical imaging system; and wherein the second model is based on a desired acquisition view, and one or more breast anatomical features of a breast in the imaging volume.

* * * * *